(12) United States Patent
Sookraj et al.

(10) Patent No.: US 11,807,613 B2
(45) Date of Patent: Nov. 7, 2023

(54) INTEGRATED METHODS FOR CHEMICAL SYNTHESIS

(71) Applicant: Novomer, Inc., Rochester, NY (US)

(72) Inventors: Sadesh H. Sookraj, Rochester, NY (US); Michael A. Slowik, Waltham, MA (US)

(73) Assignee: Novomer, Inc., Rochester, NY (US)

( * ) Notice: Subject to any disclaimer, the term of this patent is extended or adjusted under 35 U.S.C. 154(b) by 133 days.

(21) Appl. No.: 17/386,627

(22) Filed: Jul. 28, 2021

(65) Prior Publication Data

US 2021/0403446 A1 Dec. 30, 2021

Related U.S. Application Data

(63) Continuation of application No. 16/453,775, filed on Jun. 26, 2019, now Pat. No. 11,078,172, which is a continuation of application No. 15/550,300, filed as application No. PCT/US2016/017881 on Feb. 12, 2016, now abandoned.

(60) Provisional application No. 62/116,109, filed on Feb. 13, 2015.

(51) Int. Cl.
| | |
|---|---|
| *C07D 305/12* | (2006.01) |
| *C07D 307/60* | (2006.01) |
| *C01B 3/50* | (2006.01) |
| *C10G 2/00* | (2006.01) |

(52) U.S. Cl.
CPC .............. *C07D 305/12* (2013.01); *C01B 3/50* (2013.01); *C07D 307/60* (2013.01); *C10G 2/30* (2013.01); *C01B 2203/062* (2013.01); *C01B 2203/066* (2013.01); *Y02E 50/30* (2013.01); *Y02P 20/10* (2015.11)

(58) Field of Classification Search
CPC ...... C07D 305/12; C07D 307/60; C01B 3/50; C01B 2203/062; C01B 2203/066; C01B 2203/068; C01B 3/32; C01B 3/34; C10G 2/30; Y02E 50/30; Y02P 20/10; C10J 2300/1656
USPC .......................... 518/702; 549/273, 233, 328
See application file for complete search history.

(56) References Cited

U.S. PATENT DOCUMENTS

| | | | |
|---|---|---|---|
| 2,245,404 A | 6/1941 | Kise et al. | |
| 2,302,321 A | 11/1942 | Hopff et al. | |
| 2,469,704 A | 5/1949 | Stone | |
| 2,526,554 A | 10/1950 | Gresham et al. | |
| 3,002,017 A | 9/1961 | Wearsch et al. | |
| 3,326,938 A | 6/1967 | Wagner | |
| 3,751,435 A | 8/1973 | van der Ven et al. | |
| 3,800,006 A | 3/1974 | Katayama et al. | |
| 3,885,155 A | 5/1975 | Anbar | |
| 5,310,948 A | 5/1994 | Drent et al. | |
| 5,359,081 A | 10/1994 | Drent et al. | |
| 5,438,194 A | 8/1995 | Koudijs et al. | |
| 5,661,299 A | 8/1997 | Purser | |
| 5,731,252 A | 3/1998 | Warner et al. | |
| 6,147,126 A | 11/2000 | DeGeorge et al. | |
| 6,392,078 B1 | 5/2002 | Ryu et al. | |
| 6,492,535 B1 | 12/2002 | Castiglioni et al. | |
| 6,573,340 B1 | 6/2003 | Khemani et al. | |
| 6,773,578 B1 | 8/2004 | O'Rear et al. | |
| 6,852,865 B2 | 2/2005 | Coates et al. | |
| 6,916,951 B2 | 7/2005 | Tustin et al. | |
| 8,445,703 B2 | 5/2013 | Allen et al. | |
| 8,481,756 B1 | 7/2013 | Coates et al. | |
| 8,796,475 B2 | 8/2014 | Allen et al. | |
| 9,096,510 B2 | 8/2015 | Porcelli et al. | |
| 9,156,803 B2 | 10/2015 | Allen et al. | |
| 9,206,144 B2 | 12/2015 | Allen et al. | |
| 9,327,280 B2 | 5/2016 | Lee et al. | |
| 9,403,788 B2 | 8/2016 | Lee et al. | |
| 9,493,391 B2 | 11/2016 | Allen et al. | |
| 9,738,784 B2 | 8/2017 | Allen et al. | |
| 9,914,689 B2 | 3/2018 | Porcelli et al. | |
| 10,065,914 B1 | 9/2018 | Ruhl et al. | |
| 10,099,988 B2 | 10/2018 | Farmer et al. | |
| 10,099,989 B2 | 10/2018 | Sookraj | |
| 10,144,802 B2 | 12/2018 | Sookraj | |
| 10,221,150 B2 | 3/2019 | Farmer et al. | |
| 10,221,278 B2 | 3/2019 | Lee et al. | |
| 10,245,559 B2 | 4/2019 | Lapointe et al. | |
| 2003/0098274 A1 | 5/2003 | Lee et al. | |
| 2003/0162961 A1 | 8/2003 | Coates et al. | |
| 2004/0102532 A1 | 5/2004 | Landis et al. | |
| 2005/0014977 A1 | 1/2005 | Drent et al. | |
| 2005/0196343 A1 | 9/2005 | Reddy et al. | |

(Continued)

FOREIGN PATENT DOCUMENTS

| | | | |
|---|---|---|---|
| CN | 103822811 A | 5/2014 | |
| DE | 57-14596 A | 1/1982 | |

(Continued)

OTHER PUBLICATIONS

Non-Final Office Action received for U.S. Appl. No. 15/314,429, dated Mar. 19, 2019, 10 pages.

Dubinsky et al., "Thermal Degradation of Poly (acrylic acid) Containing Copper Nitrate", Polymer Degradation and Stability, vol. 86, 2004, pp. 171-178.

Extended European Search Report (includes Supplementary European Search Report and Search Opinion) received for European Patent Application No. 16750026.3, dated Sep. 19, 2018, 11 pages.

(Continued)

*Primary Examiner* — Taylor V Oh
(74) *Attorney, Agent, or Firm* — Young Basile Hanlon & MacFarlane, P.C.

(57) ABSTRACT

The integrated processes herein provide improved carbon efficiency for processes based on coal or biomass gasification or steam methane reforming. Provided are also ethylene oxide carbonylation products such as beta-propiolactone and succinic anhydride having a bio-based content between 0% and 100%, and methods for producing and analyzing the same.

20 Claims, 9 Drawing Sheets

(56) References Cited

U.S. PATENT DOCUMENTS

| | | |
|---|---|---|
| 2005/0209411 A1 | 9/2005 | Nestler et al. |
| 2005/0222458 A1 | 10/2005 | Craciun et al. |
| 2005/0240032 A1 | 10/2005 | Luinstra et al. |
| 2007/0155984 A1 | 7/2007 | Sielcken et al. |
| 2007/0217965 A1 | 9/2007 | Johnson et al. |
| 2007/0225522 A1 | 9/2007 | Kobayashi et al. |
| 2007/0293695 A1 | 12/2007 | Zoeller et al. |
| 2009/0075295 A1 | 3/2009 | Lindsey |
| 2009/0124787 A1 | 5/2009 | Preishuber-Pflugl et al. |
| 2009/0173694 A1 | 7/2009 | Peinemann et al. |
| 2009/0178495 A1 | 7/2009 | Steigmiller et al. |
| 2009/0253934 A1 | 10/2009 | Ho et al. |
| 2009/0287000 A1 | 11/2009 | Coates et al. |
| 2009/0299032 A1 | 12/2009 | Allen |
| 2010/0323573 A1 | 12/2010 | Chu et al. |
| 2010/0323885 A1 | 12/2010 | Herfert et al. |
| 2011/0065894 A1 | 3/2011 | Allen |
| 2011/0226697 A1 | 9/2011 | McLellan et al. |
| 2011/0319849 A1 | 12/2011 | Collias et al. |
| 2012/0108695 A1 | 5/2012 | Won et al. |
| 2012/0123137 A1 | 5/2012 | Allen et al. |
| 2012/0189861 A1 | 7/2012 | Matsumoto et al. |
| 2012/0202951 A1 | 8/2012 | Gartner et al. |
| 2013/0004454 A1 | 1/2013 | Weiss et al. |
| 2013/0072645 A1 | 3/2013 | Balduf et al. |
| 2013/0165670 A1 | 6/2013 | Allen et al. |
| 2013/0209775 A1 | 8/2013 | Allen et al. |
| 2013/0274697 A1 | 10/2013 | Godlewski et al. |
| 2013/0281715 A1 | 10/2013 | Allen et al. |
| 2013/0299417 A1 | 11/2013 | Luchinger et al. |
| 2014/0018570 A1 | 1/2014 | Pazicky et al. |
| 2014/0018574 A1 | 1/2014 | Raith et al. |
| 2014/0275575 A1 | 9/2014 | Allen et al. |
| 2014/0296522 A1 | 10/2014 | Lee et al. |
| 2014/0309399 A1 | 10/2014 | Porcelli et al. |
| 2015/0005513 A1 | 1/2015 | Lee et al. |
| 2015/0141693 A1 | 5/2015 | Allen et al. |
| 2015/0299083 A1 | 10/2015 | Porcelli et al. |
| 2015/0368394 A1 | 12/2015 | Allen |
| 2016/0016876 A1 | 1/2016 | Mahoney |
| 2016/0102040 A1 | 4/2016 | Allen et al. |
| 2016/0102068 A1 | 4/2016 | Allen et al. |
| 2016/0204465 A1 | 7/2016 | Mimura et al. |
| 2016/0288057 A1 | 10/2016 | Lapointe et al. |
| 2017/0029352 A1 | 2/2017 | Sookraj et al. |
| 2017/0073463 A1 | 3/2017 | Lee et al. |
| 2017/0080409 A1 | 3/2017 | Farmer et al. |
| 2017/0096407 A1 | 4/2017 | Sookraj |
| 2017/0107103 A1 | 4/2017 | Sookraj et al. |
| 2017/0145126 A1 | 5/2017 | Mahoney |
| 2017/0225157 A1 | 8/2017 | Lee |
| 2017/0247309 A1 | 8/2017 | Porcelli et al. |
| 2017/0267618 A1 | 9/2017 | Sookraj et al. |
| 2018/0016219 A1 | 1/2018 | Farmer et al. |
| 2018/0022677 A1 | 1/2018 | Sookraj |
| 2018/0029005 A1 | 2/2018 | Sookraj |
| 2018/0030014 A1 | 2/2018 | Sookraj et al. |
| 2018/0030015 A1 | 2/2018 | Farmer et al. |
| 2018/0030201 A1 | 2/2018 | Farmer et al. |
| 2018/0057619 A1 | 3/2018 | Sookraj |
| 2018/0094100 A1 | 4/2018 | Farmer et al. |
| 2018/0153746 A1 | 6/2018 | Sookraj |
| 2018/0155490 A1 | 6/2018 | Sookraj |
| 2018/0155491 A1 | 6/2018 | Sookraj |
| 2018/0282251 A1 | 10/2018 | Sookraj |
| 2018/0305286 A1 | 10/2018 | Sookraj |
| 2018/0305289 A1 | 10/2018 | Sookraj et al. |
| 2018/0354881 A1 | 12/2018 | Farmer et al. |
| 2018/0354882 A1 | 12/2018 | Sookraj |
| 2019/0002293 A1 | 1/2019 | Sookraj et al. |
| 2019/0002385 A1 | 1/2019 | Sookraj et al. |
| 2019/0002400 A1 | 1/2019 | Sookraj |
| 2019/0030520 A1 | 1/2019 | Lee |
| 2019/0031592 A1 | 1/2019 | Sookraj et al. |
| 2019/0047972 A1 | 2/2019 | Sookraj |
| 2019/0071538 A1 | 3/2019 | Sookraj |
| 2019/0076834 A1 | 3/2019 | Sookraj |
| 2019/0076835 A1 | 3/2019 | Sookraj |
| 2019/0106532 A1 | 4/2019 | Sookraj |

FOREIGN PATENT DOCUMENTS

| | | |
|---|---|---|
| EP | 0352850 A1 | 1/1990 |
| EP | 0441447 A1 | 8/1991 |
| EP | 2325214 A1 | 5/2011 |
| GB | 762138 A | 11/1956 |
| NO | 2017/165344 A1 | 9/2017 |
| WO | 2003/050154 A2 | 6/2003 |
| WO | 2003/074585 A1 | 9/2003 |
| WO | 2010/118128 A1 | 10/2010 |
| WO | 2010/137974 A1 | 12/2010 |
| WO | 2011/123558 A1 | 10/2011 |
| WO | 2011/163309 A2 | 12/2011 |
| WO | 2012/030619 A1 | 3/2012 |
| WO | 2012/051219 A2 | 4/2012 |
| WO | 2012/158573 A1 | 11/2012 |
| WO | 2013/063191 A1 | 5/2013 |
| WO | 2013/067460 A1 | 5/2013 |
| WO | 2013/122905 A1 | 8/2013 |
| WO | 2013/126375 A1 | 8/2013 |
| WO | 2013/185009 A1 | 12/2013 |
| WO | 2014/004858 A1 | 1/2014 |
| WO | 2014/008232 A2 | 1/2014 |
| WO | 2014150387 A1 | 9/2014 |
| WO | 2015/085295 A2 | 6/2015 |
| WO | 2015/110321 A1 | 7/2015 |
| WO | 2015/138975 A1 | 9/2015 |
| WO | 2015/171372 A1 | 11/2015 |
| WO | 2015/184289 A1 | 12/2015 |
| WO | 2016/015019 A1 | 1/2016 |
| WO | 2016/130947 A1 | 8/2016 |
| WO | 2016/130977 A1 | 8/2016 |
| WO | 2016/130988 A1 | 8/2016 |
| WO | 2016/130993 A1 | 8/2016 |
| WO | 2016/130998 A1 | 8/2016 |
| WO | 2016/131001 A1 | 8/2016 |
| WO | 2016/131003 A1 | 8/2016 |
| WO | 2016/131004 A1 | 8/2016 |
| WO | 2017/023777 A1 | 2/2017 |
| WO | 2017/023820 A1 | 2/2017 |
| WO | 2017/165323 A1 | 9/2017 |
| WO | 2017/165345 A1 | 9/2017 |
| WO | 2018/085251 A1 | 5/2018 |
| WO | 2018/085254 A1 | 5/2018 |
| WO | 2018/106824 A1 | 6/2018 |
| WO | 2018/107185 A1 | 6/2018 |
| WO | 2018/136638 A1 | 7/2018 |
| WO | 2018/144998 A1 | 8/2018 |
| WO | 2018/170006 A1 | 9/2018 |
| WO | 2018/200471 A1 | 11/2018 |
| WO | 2019/006366 A1 | 1/2019 |
| WO | 2019/006377 A1 | 1/2019 |
| WO | 2019/050649 A1 | 3/2019 |
| WO | 2019/051184 A1 | 3/2019 |
| WO | 2019/070981 A1 | 4/2019 |

OTHER PUBLICATIONS

Extended European Search Report received for European Patent Application No. 15799546.5, dated Nov. 24, 2017, 6 pages.
Ganji et al., "In Situ Generation of the Coates Catalyst: a Practical and Versatile Catalytic System for the Carbonylation of Meso-Epoxides", ChemInform Abstract, vol. 42, 2011, 1 page.
Ganji et al., "In Situ Generation of the Coates Catalyst: A Practical and Versatile Catalytic System for the Carbonylation of Meso-Epoxides", Organic Letters, vol. 13, Jun. 17, 2011, pp. 3142-3145.
Getzler et al., "Synthesis of 13-Lactones: A Highly Active and Selective Catalyst for Epoxide Carbonylation", Journal of the American Chemical Society. vol. 124, No. 7, 2002, pp. 1174-1175.
International Preliminary Report on Patentability received for PCT Patent Application No. PCT/US2015/033232, dated Dec. 15, 2016, 7 Pages.

(56) References Cited

OTHER PUBLICATIONS

International Preliminary Report on Patentability received for PCT Patent Application No. PCT/US2016/017881, dated Aug. 24, 2017, 7 pages.
International Search Report and Written Opinion received for PCT Patent Application No. PCT/US2016/017881, dated May 2, 2016, 8 pages.
International Search Report and Written Opinion for PCT Patent Application No. PCT/US2016/017875 dated May 6, 2016, 11 pages.
International Search Report and Written Opinion received for PCT Application No. PCT/US2016/017844, dated May 6, 2016, 10 Pages.
International Search Report and Written Opinion received for PCT Patent Application No. PCT/US13/25683, dated Apr. 23, 2013, 8 pages.
International Search Report and Written Opinion received for PCT Patent Application No. PCT/US17/23302, dated Jun. 5, 2017, 9 pages.
International Search Report and Written Opinion received for PCT Patent Application No. PCT/US17/23303, dated Jun. 7, 2017, 13 pages.
International Search Report and Written Opinion received for PCT Patent Application No. PCT/US2010/030230, dated Jun. 10, 2010, 17 pages.
International Search Report and Written Opinion received for PCT Patent Application No. PCT/US2011/049125, dated Jan. 11, 2012, 10 pages.
International Search Report and Written Opinion received for PCT Patent Application No. PCT/US2012/037675, dated Aug. 9, 2012, 12 pages.
International Search Report and Written Opinion received for PCT Patent Application No. PCT/US2012/061791, dated Feb. 8, 2013, 10 pages.
International Search Report and Written Opinion received for PCT Patent Application No. PCT/US2013/026810, dated Apr. 30, 2013, 8 pages.
International Search Report and Written Opinion received for PCT Patent Application No. PCT/US2013/048238, dated Dec. 3, 2013, 8 pages.
International Search Report and Written Opinion received for PCT Patent Application No. PCT/US2013/049026, dated Dec. 17, 2013, 9 pages.
International Search Report and Written Opinion received for PCT Patent Application No. PCT/US2014/069066, dated Mar. 16, 2015, 10 pages.
International Search Report and Written Opinion received for PCT Patent Application No. PCT/US2015/020562, dated Jun. 18, 2015, 9 pages.
International Search Report and Written Opinion received for PCT Patent Application No. PCT/US2015/028123, dated Jul. 23, 2015, 7 pages.
International Search Report and Written Opinion received for PCT Patent Application No. PCT/US2015/033232, dated Aug. 19, 2015, 8 pages.
International Search Report and Written Opinion received for PCT Patent Application No. PCT/US2015/042124, dated Dec. 15, 2015, 14 pages.
International Search Report and Written Opinion received for PCT Patent Application No. PCT/US2016/017797, dated May 5, 2016, 9 pages.
International Search Report and Written Opinion received for PCT Patent Application No. PCT/US2016/017861, dated Apr. 29, 2016, 25 pages.
International Search Report and Written Opinion received for PCT Patent Application No. PCT/US2016/017868, dated May 2, 2016, 9 pages.
International Search Report and Written Opinion received for PCT Patent Application No. PCT/US2016/017878, dated May 2, 2016, 9 pages.
International Search Report and Written Opinion received for PCT Patent Application No. PCT/US2016/017880, dated Apr. 29, 2016, 9 pages.
International Search Report and Written Opinion received for PCT Patent Application No. PCT/US2016/044772, dated Nov. 8, 2016, 17 pages.
International Search Report and Written Opinion received for PCT Patent Application No. PCT/US2016/044927, dated Nov. 8, 2016, 17 pages.
International Search Report and Written Opinion received for PCT Patent Application No. PCT/US2017/059243, dated Feb. 1, 2018, 10 pages.
Kaesz et al., "Hydride Complexes of the Transition Metals", Chemical Reviews, vol. 72, No. 3, 1972, pp. 231-281.
Non-Final Office Action received for U.S. Appl. No. 15/550,300, dated Dec. 31, 2018, 11 pages.
Partial Supplementary European Search Report received for European Patent Application No. 16750026.3, dated Jul. 12, 2018, 10 pages.
Rowley et al., "Catalytic Double Carbonylation of Epoxides to Succinic Anhydrides: Catalyst Discovery, Reaction Scope, and Mechanism", Journal of the American Chemical Society, vol. 129, No. 16, 2007, pp. 4948-4960.
Schechtman et al, "Chemical Synthesis of Isotactic Poly(3-Hydroxyalkanoates)", Polymer Preprints, Division Of Polymer Chemistry, Inc., vol. 40, No. 1, 1999, pp. 508-509.
Schulz, Hans, "Short History and Present Trends of Fischer-Tropsch Synthesis", Applied Catalysis A: General, vol. 186, 1999, pp. 3-12.
Slowik et al., "Catalytic Conversion of Waste Carbon Monoxide to Valuable Chemicals & Materials", Technical Proceedings of the Clean Technology Conference and Trade Show, 2010, pp. 283-286.
Stanghellini et al., "Redox Reactions of Metal Carbonyls. I. Kinetics and Mechanism of Disproportionation of Co2(Co)8 with Piperidine", Inorganica Chimica Acta, vol. 22, 1977, pp. 19-22.
Trimm, D. L., "Minimisation of Carbon Monoxide in a Hydrogen Stream for Fuel Cell Application", Applied Catalysis A: General, vol. 296, 2005, 11 pages.
"Understanding Biobased Carbon Content", Society or the Plastics Industry Bioplastics Council, Feb. 2012, 14 pages.
Wilen et al., "Strategies in Optical Resolutions", Tetrahedron Report No. 38, vol. 33, 1977, pp. 2725-2736.

1 carbon from CO via syngas upgrade  2 carbons from ethylene via MTO 1 carbon from CO via syngas upgrade  2 carbons from ethylene via MTO 2 carbons from CO via syngas upgrade 2 carbons from ethylene via MTO 1 carbonyl carbon from CO (bio-based or fossil)

2 non-carbonyl carbons from EO (bio-based or fossil)

Each carbonyl carbon individually derived from CO (bio-based or fossil)

2 non-carbonyl carbons from EO (bio-based or fossil)

INTEGRATED METHODS FOR CHEMICAL SYNTHESIS

CROSS-REFERENCE TO RELATED APPLICATIONS

This application is a continuation of U.S. patent application Ser. No. 16/453,775 filed Jun. 26, 2019, which is a continuation of U.S. patent application Ser. No. 15/550,300, filed Aug. 10, 2017, which is a U.S. National Phase Patent Application of PCT/US2016/17881, filed Feb. 12, 2016, which claims priority to and benefit of U.S. Provisional Patent Application No. 62/116,109, filed Feb. 13, 2015, each of which is incorporated herein by reference in its entirety.

FIELD

The present disclosure relates generally to the integrated production of chemicals, and more specifically to integrated processes that provide improved carbon efficiency for processes based on coal or biomass gasification or steam methane reforming. The present disclosure also relates to ethylene oxide carbonylation products, such as beta-propiolactone and succinic anhydride having a bio-based content, and methods for producing and analyzing thereof.

BACKGROUND

Interest in finding sustainable methods to produce energy and chemicals continues to increase in the face of concerns that anthropogenic carbon emissions are responsible for global climate change. Among the options being considered is the use of biomass to feed chemical production via gasification. This process has appeal since the processes first developed more than a century ago for coal gasification can be applied to practically any biomass input and the subsequent conversion of the resulting syngas to fuels and chemicals is a well-established process with the potential to provide a diverse range of chemical products.

However, a drawback to gasification technology is that it is relatively inefficient in terms of the percentage of the carbon input to the gasifier that is actually incorporated into end products. This is due in large part to the fact that coal and biomass-derived syngas has a low $H_2$ to CO ratio (typically around ~0.7) and must be upgraded by water gas shift reaction (WGSR) prior to utilization in downstream processes such as Fischer Tropsch (FT) or methanol-to-olefins (MTO) synthesis that requires an $H_2$:CO ratio around 2. The water gas shift process consumes a portion of the carbon monoxide in the syngas releasing $CO_2$ and providing additional hydrogen.

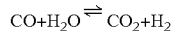

$$CO + H_2O \rightleftharpoons CO_2 + H_2$$

The resulting $CO_2$ (22 kg $CO_2$ per kg of $H_2$ produced) is emitted to the atmosphere and erodes the carbon efficiency and environmental benefit of biomass gasification technologies.

A related situation exists for conversion of carbonaceous feedstocks to produce pure hydrogen streams for use in chemical production (e.g., ammonia production) or for use as a fuel. Here, the preferred process is methane steam reforming (MSR): $CH_4 + H_2O \rightleftharpoons CO + 3 H_2$. Again, the gas stream produced by MSR is typically treated by WGSR to increase the hydrogen content resulting in $CO_2$ emissions.

Typical routes to C3 and C4 chemicals require that all of the carbon atoms in the molecules produced be derived wholly from either bio-based or fossil sources. Accordingly, there is also a need for methods of producing chemicals such as beta-propiolactone (BPL) and succinic anhydride (SA) in such a way that they contain a known and controllable content of bio-based materials. Furthermore, existing methods used to produce bio-based BPL and SA at scale rely on the availability of bio-based supplies of C3 feedstocks such as propene, which are not economically competitive with fossil sources.

It is also a challenge to determine which feedstocks were used to produce a given batch of beta-propiolactone or succinic anhydride, as once the chemicals are produced, any sample of BPL or SA is largely indistinguishable. Standards bodies, secondary manufacturers, and end consumers are increasingly concerned with the source of the products they use, and particularly the bio-based content of the chemicals used to make those products. Accordingly, methods for determining the bio-based content of the chemicals used to produce BPL, SA, and their downstream products are needed.

BRIEF SUMMARY

The methods and systems described herein address the various challenges known in the art with respect to producing various bio-based chemicals. For example, epoxide carbonylation can be performed industrially utilizing syngas streams containing hydrogen, carbon monoxide and varying amounts carbon dioxide. However, contrary to expectation, the epoxide carbonylation reaction proceeds selectively in the presence of these mixed gas streams and incorporates excess CO from the syngas stream into valuable chemical precursors. This is economically and environmentally preferable to performing WGSR which releases the excess carbon as $CO_2$. The integrated processes herein therefore provide improved carbon efficiency for processes based on coal or biomass gasification or steam methane reforming.

In one aspect, provided is an integrated process for the conversion of biomass or coal to FT products and commodity chemicals derived from epoxide carbonylation. In certain embodiments, such methods comprise:

a) in a first reaction zone, contacting syngas derived from gasification of biomass or coal with an epoxide in the presence of a carbonylation catalyst thereby consuming carbon monoxide from the syngas and producing an epoxide carbonylation product, b) recovering an upgraded gas stream from the first reaction zone wherein the upgraded gas stream has a higher hydrogen to carbon monoxide ratio than the starting syngas stream, c) in a second reaction zone, utilizing the upgraded gas stream to conduct a second chemical process requiring a hydrogen to carbon monoxide ratio higher than the ratio in the industrial gas stream utilized in step (a).

In certain embodiments of the method above, the second chemical process comprises Fischer Tropsch synthesis.

In a second aspect, provided is an integrated process for the production of hydrogen and commodity chemicals derived from epoxide carbonylation. In certain embodiments, such methods comprise:

a) in a first reaction zone, contacting a syngas stream derived from methane steam reforming with an epoxide in the presence of a carbonylation catalyst thereby consuming carbon monoxide from the syngas stream and producing an epoxide carbonylation product, b) recovering an upgraded gas stream from the first reaction zone wherein the upgraded gas stream has a higher hydrogen to carbon monoxide ratio than the starting syngas stream, and c) in a second reaction zone, utilizing the upgraded gas stream to conduct a second chemical process requiring a hydrogen to carbon monoxide ratio higher than the ratio in the industrial gas stream utilized in step (a).

In certain embodiments, the epoxide carbonylation product produced in step (a) of the methods above is selected from the group consisting of: optionally substituted beta propiolactone, optionally substituted succinic anhydride, and optionally substituted polypropiolactone. In certain embodiments, the epoxide in the methods above is ethylene oxide and the epoxide carbonylation product is selected from the group consisting of: beta propiolactone (BPL), succinic anhydride (SA), and polypropiolactone (PPL). In certain embodiments, the epoxide in the methods above is propylene oxide and the epoxide carbonylation product is selected from the group consisting of: beta butyrolactone, methyl succinic anhydride and poly(3-hydroxy butyrate).

In certain embodiments of the methods above, the syngas stream in step (a) is characterized in that it has an $H_2$ to CO ratio less than 1.2. In certain embodiments, the upgraded gas stream in step (b) is characterized in that it has an $H_2$ to CO ratio greater than 1.9.

In another aspect, provided is an integrated process for the production of hydrogen and commodity chemicals derived from beta lactone carbonylation. In certain embodiments, such methods comprise:

a) in a first reaction zone, contacting syngas with a beta propiolactone in the presence of a carbonylation catalyst thereby consuming carbon monoxide from the syngas and producing a succinic anhydride product, b) recovering an upgraded gas stream from the first reaction zone wherein the upgraded gas stream has a higher hydrogen to carbon monoxide ratio than the starting syngas stream, c) in a second reaction zone, utilizing the upgraded gas stream to conduct a second chemical process requiring a hydrogen to carbon monoxide ratio higher than the ratio in the industrial gas stream utilized in step (a).

In certain embodiments of this aspect, the syngas in step (a) is derived from methane steam reforming (MSR). In certain embodiments, the syngas in step (a) is an upgraded gas stream produced as described in the first two aspects of the methods described above.

In certain embodiments of this aspect, the beta propiolactone carbonylation reaction zone is operated under conditions such that substantially all of the CO in the syngas stream is consumed.

In some embodiments, provided are ethylene oxide carbonylation products (such as BPL and SA), produced by carbonylation of ethylene oxide wherein the bio-based content of the ethylene carbonylation products are between 0% and 100% (non-inclusive).

In some embodiments, provided is a process for producing ethylene oxide carbonylation products (such as BPL and SA) having a bio-based content greater than 0% and less than 100%, comprising carbonylating ethylene oxide using carbon monoxide, wherein one of the ethylene oxide and carbon monoxide has a bio-based content greater than 0%, and the other has a bio-based content of less than 100%.

In some embodiments, provided is a method for determining whether a sample of BPL was produced from a combination of bio-based and fossil carbon synthons, comprising thermally decomposing the BPL to ethylene and carbon dioxide; determining the isotopic abundance of $^{14}C$ in the carbon dioxide carbon; and determining the isotopic abundance of $^{14}C$ in the ethylene carbons.

In some embodiments, provided is a method for determining whether a sample of SA was produced from a combination of bio-based and fossil carbon synthons, comprising thermally decomposing the SA to γ-ketopimelic acid and carbon dioxide; determining the isotopic abundance of $^{14}C$ in the carbon dioxide carbon; and determining the isotopic abundance of $^{14}C$ in the γ-ketopimelic acid carbons.

In some embodiments, provided is a method for determining whether a sample of polyacrylic acid (PAA) was produced from a combination of bio-based and fossil carbon synthons, comprising thermally decomposing the PAA in the presence of a catalyst to carbon dioxide and a residue; determining the isotopic abundance of $^{14}C$ in the carbon dioxide, and determining the isotopic abundance of $^{14}C$ in the residue.

In some aspects, provided is beta-propiolactone produced by carbonylation of ethylene oxide having a pMC of zero, as defined by ASTM D6866, using carbon monoxide having a pMC greater than zero, as defined by ASTM D6866. In other aspects, provided is beta-propiolactone produced by carbonylation of ethylene oxide having a pMC greater than zero, as defined by ASTM D6866, using carbon monoxide having a pMC of zero, as defined by ASTM D6866. In certain aspects, provided is beta-propiolactone produced by carbonylation of ethylene oxide using carbon monoxide, wherein one of the ethylene oxide and carbon monoxide has a biobased content greater than zero percent, and the other has a biobased content of less than 100 percent. In some variations, provided is beta propiolactone, wherein two of the three carbon atoms in the beta propiolactone are bio-based and the third carbon atom is fossil-based. In other aspects, provided is beta propiolactone, wherein one of the three carbon atoms in the beta propiolactone is bio-based and the other two carbons atom are fossil-based.

In other aspects, provided is succinic anhydride produced by carbonylation of ethylene oxide having a pMC greater than zero, as defined by ASTM D6866, using carbon monoxide having a pMC of zero, as defined by ASTM D6866. In other aspects, provided is Succinic anhydride produced by carbonylation of ethylene oxide using carbon monoxide, wherein one of the ethylene oxide and carbon monoxide has a biobased content greater than zero percent, and the other has a biobased content of less than 100 percent. In some variations, provided is succinic anhydride, wherein two of the four carbon atoms of the succinic anhydride are bio-based and two of the carbon atoms are fossil-based.

BRIEF DESCRIPTION OF THE FIGURES

The present application can be best understood by reference to the following description taken in conjunction with the accompanying figures, in which like parts may be referred to by like numerals.

DEFINITIONS

Figure 1:
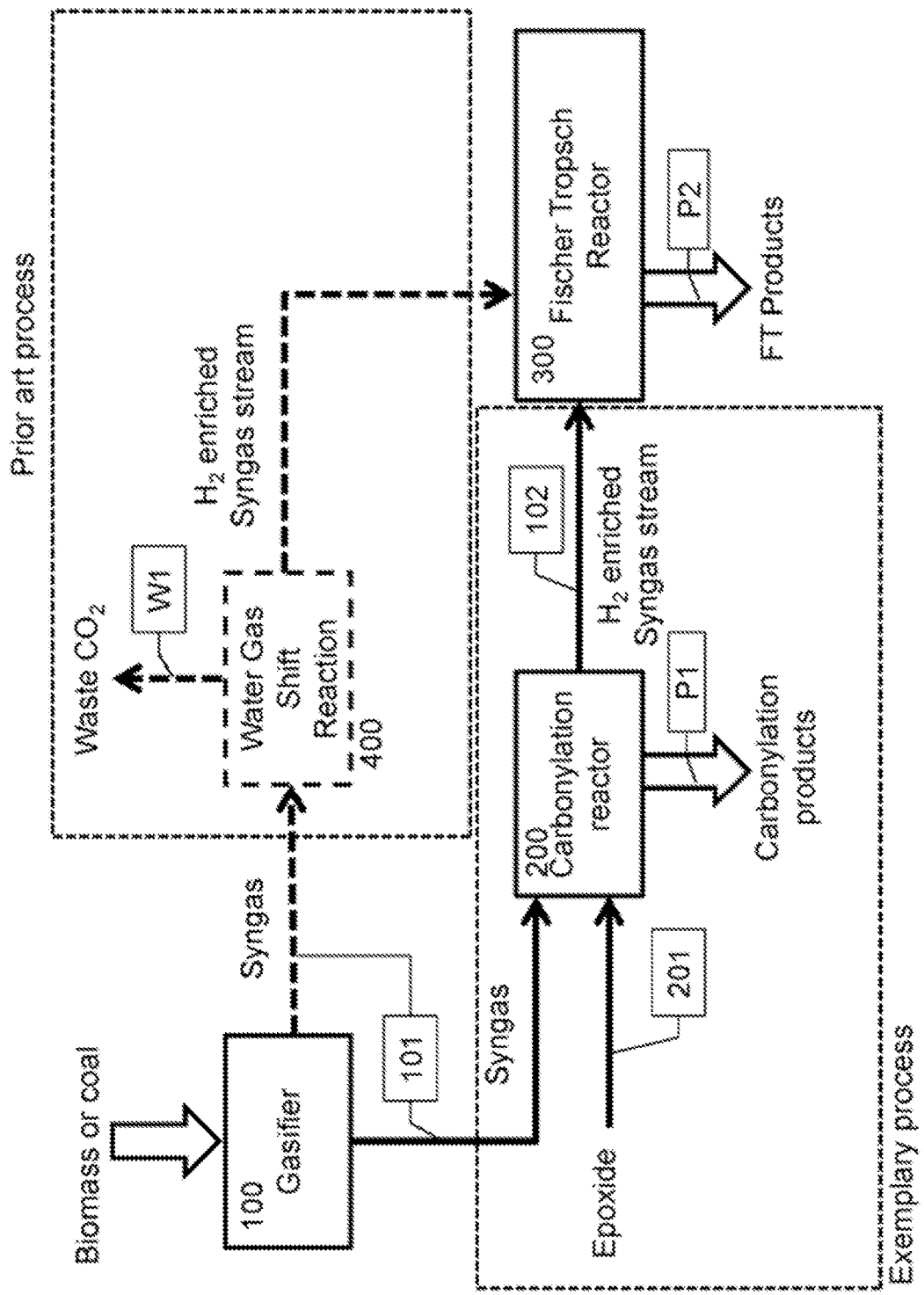
FIG. 1 shows a schematic of an exemplary integrated process for the conversion of biomass or coal to synthesis gas and commodity chemicals or polymers derived from epoxide carbonylation.

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987.

Certain compounds herein can comprise one or more asymmetric centers, and thus can exist in various stereoisomeric forms, e.g., enantiomers and/or diastereomers. Thus, compounds and compositions thereof may be in the form of an individual enantiomer, diastereomer or geometric isomer, or may be in the form of a mixture of stereoisomers. In certain embodiments, the compounds herein are enantiopure compounds. In certain other embodiments, mixtures of enantiomers or diastereomers are provided.

Furthermore, certain compounds, as described herein may have one or more double bonds that can exist as either a Z or E isomer, unless otherwise indicated. In some variations, the compounds include individual isomers substantially free of other isomers and alternatively, as mixtures of various isomers, e.g., racemic mixtures of enantiomers. In addition to the above-mentioned compounds per se, provided are also compositions comprising one or more compounds.

As used herein, the term "isomers" includes any and all geometric isomers and stereoisomers. For example, "isomers" include cis- and trans-isomers, E- and Z-isomers, R- and S-enantiomers, diastereomers, (D)-isomers, (L)-isomers, racemic mixtures thereof, and other mixtures thereof, as falling within the scope herein. For instance, a compound may, in some embodiments, be provided substantially free of one or more corresponding stereoisomers, and may also be referred to as "stereochemically enriched."

Where a particular enantiomer is preferred, it may, in some embodiments be provided substantially free of the opposite enantiomer, and may also be referred to as "optically enriched." "Optically enriched," as used herein, means that the compound is made up of a significantly greater proportion of one enantiomer. In certain embodiments the compound is made up of at least about 90% by weight of an enantiomer. In some embodiments the compound is made up of at least about 95%, 97%, 98%, 99%, 99.5%, 99.7%, 99.8%, or 99.9% by weight of an enantiomer. In some embodiments the enantiomeric excess of provided compounds is at least about 90%, 95%, 97%, 98%, 99%, 99.5%, 99.7%, 99.8%, or 99.9%. In some embodiments, enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, N.Y., 1962); Wilen, S. H. *Tables of Resolving Agents and Optical Resolutions* p. 268 (E. L. Eliel, Ed., Univ. of Notre Dame Press, Notre Dame, IN 1972).

The terms "halo" and "halogen" as used herein refer to an atom selected from fluorine (fluoro, —F), chlorine (chloro, —Cl), bromine (bromo, —Br), and iodine (iodo, —I).

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. In some variations, the aliphatic group is unbranched or branched. In other variations, the aliphatic group is cyclic. Unless otherwise specified, in some variations, aliphatic groups contain 1-30 carbon atoms. In certain embodiments, aliphatic groups contain 1-12 carbon atoms. In certain embodiments, aliphatic groups contain 1-8 carbon atoms. In certain embodiments, aliphatic groups contain 1-6 carbon atoms. In some embodiments, aliphatic groups contain 1-5 carbon atoms, in some embodiments, aliphatic groups contain 1-4 carbon atoms, in yet other embodiments aliphatic groups contain 1-3 carbon atoms, and in yet other embodiments aliphatic groups contain 1-2 carbon atoms. Suitable aliphatic groups include, for example, linear or branched, alkyl, alkenyl, and alkynyl groups, and hybrids thereof such as (cycloalkyl) alkyl, (cycloalkenyl)alkyl or (cycloalkyl)alkenyl.

The term "heteroaliphatic," as used herein, refers to aliphatic groups wherein one or more carbon atoms are independently replaced by one or more atoms selected from the group consisting of oxygen, sulfur, nitrogen, phosphorus, or boron. In certain embodiments, one or two carbon atoms are independently replaced by one or more of oxygen, sulfur, nitrogen, or phosphorus. Heteroaliphatic groups may be substituted or unsubstituted, branched or unbranched, cyclic or acyclic, and include "heterocycle," "heterocyclyl," "heterocycloaliphatic," or "heterocyclic" groups. In some variations, the heteroaliphatic group is branched or unbranched. In other variations, the heteroaliphatic group is cyclic. In yet other variations, the heteroaliphatic group is acyclic.

In some variations, the term "epoxide", as used herein, refers to a substituted or unsubstituted oxirane. Substituted oxiranes include monosubstituted oxiranes, disubstituted oxiranes, trisubstituted oxiranes, and tetrasubstituted oxiranes. Such epoxides may be further optionally substituted as defined herein. In certain embodiments, epoxides comprise a single oxirane moiety. In certain embodiments, epoxides comprise two or more oxirane moieties.

In some variations, the term "glycidyl", as used herein, refers to an oxirane substituted with a hydroxyl methyl group or a derivative thereof. In other variations, the term glycidyl as used herein is meant to include moieties having additional substitution on one or more of the carbon atoms of the oxirane ring or on the methylene group of the hydroxymethyl moiety, examples of such substitution may include, for example, alkyl groups, halogen atoms, and aryl groups. The terms glycidyl ester, glycidyl acrylate, and glycidyl ether denote substitution at the oxygen atom of the above-mentioned hydroxymethyl group. For example, the oxygen atom is bonded to an acyl group, an acrylate group, or an alkyl group respectively.

The term "acrylate" or "acrylates" as used herein refer to any acyl group having a vinyl group adjacent to the acyl carbonyl. The terms encompass mono-, di- and tri-substituted vinyl groups. Acrylates may include, for example, acrylate, methacrylate, ethacrylate, cinnamate (3-phenylacrylate), crotonate, tiglate, and senecioate.

The term "polymer", as used herein, refers to a molecule comprising multiple repeating units. In some variations, the polymer is a molecule of high relative molecular mass, the structure of which comprises the multiple repetition of units derived, actually or conceptually, from molecules of low relative molecular mass. In certain embodiments, a polymer is comprised of only one monomer species (e.g., polyethylene oxide). In certain embodiments, the polymer may be a copolymer, terpolymer, heteropolymer, block copolymer, or tapered heteropolymer of one or more epoxides. In one variation, the polymer may be a copolymer, terpolymer, heteropolymer, block copolymer, or tapered heteropolymer of two or more monomers.

The term "unsaturated", as used herein, means that a moiety has one or more double or triple bonds.

The terms "cycloaliphatic", "carbocycle", or "carbocyclic", used alone or as part of a larger moiety, refer to a saturated or partially unsaturated cyclic aliphatic monocyclic, bicyclic, or polycyclic ring systems, as described herein, having from 3 to 12 members, wherein the aliphatic ring system is optionally substituted as defined above and described herein. Cycloaliphatic groups include, for example, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons. The terms "cycloaliphatic", "carbocycle" or "carbocyclic" also include aliphatic rings that are fused to one or more aromatic or nonaromatic rings, such as decahydronaphthyl or tetrahydronaphthyl, where the radical or point of attachment is on the aliphatic ring. In some embodiments, a carbocyclic group is bicyclic. In some embodiments, a carbocyclic group is tricyclic. In some embodiments, a carbocyclic group is polycyclic.

The term "alkyl," as used herein, refers to a saturated hydrocarbon radical. In some variations, the alkyl group is a saturated, straight- or branched-chain hydrocarbon radicals derived from an aliphatic moiety containing between one and six carbon atoms by removal of a single hydrogen atom. Unless otherwise specified, in some variations, alkyl groups contain 1-12 carbon atoms. In certain embodiments, alkyl groups contain 1-8 carbon atoms. In certain embodiments, alkyl groups contain 1-6 carbon atoms. In some embodiments, alkyl groups contain 1-5 carbon atoms, in some embodiments, alkyl groups contain 1-4 carbon atoms, in yet other embodiments alkyl groups contain 1-3 carbon atoms, and in yet other embodiments alkyl groups contain 1-2 carbon atoms. Alkyl radicals may include, for example, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, and dodecyl.

The term "alkenyl," as used herein, denotes a monovalent group having at least one carbon-carbon double bond. In some variations, the alkenyl group is a monovalent group derived from a straight- or branched-chain aliphatic moiety having at least one carbon-carbon double bond by the removal of a single hydrogen atom. Unless otherwise specified, in some variations, alkenyl groups contain 2-12 carbon atoms. In certain embodiments, alkenyl groups contain 2-8 carbon atoms. In certain embodiments, alkenyl groups contain 2-6 carbon atoms. In some embodiments, alkenyl groups contain 2-5 carbon atoms, in some embodiments, alkenyl groups contain 2-4 carbon atoms, in yet other embodiments alkenyl groups contain 2-3 carbon atoms, and in yet other embodiments alkenyl groups contain 2 carbon atoms. Alkenyl groups include, for example, ethenyl, propenyl, butenyl, and 1-methyl-2-buten-1-yl.

The term "alkynyl," as used herein, refers to a monovalent group having at least one carbon-carbon triple bond. In some variations, the alkynyl group is a monovalent group derived from a straight- or branched-chain aliphatic moiety having at least one carbon-carbon triple bond by the removal of a single hydrogen atom. Unless otherwise specified, in some variations, alkynyl groups contain 2-12 carbon atoms. In certain embodiments, alkynyl groups contain 2-8 carbon atoms. In certain embodiments, alkynyl groups contain 2-6 carbon atoms. In some embodiments, alkynyl groups contain 2-5 carbon atoms, in some embodiments, alkynyl groups contain 2-4 carbon atoms, in yet other embodiments alkynyl groups contain 2-3 carbon atoms, and in yet other embodiments alkynyl groups contain 2 carbon atoms. Representative alkynyl groups include, for example, ethynyl, 2-propynyl (propargyl), and 1-propynyl.

The term "carbocycle" and "carbocyclic ring" as used herein, refers to monocyclic and polycyclic moieties wherein the rings contain only carbon atoms. Unless otherwise specified, carbocycles may be saturated, partially unsaturated or aromatic, and contain 3 to 20 carbon atoms. Representative carbocyles include, for example, cyclopropane, cyclobutane, cyclopentane, cyclohexane, bicyclo[2,2,1]heptane, norbornene, phenyl, cyclohexene, naphthalene, and spiro[4.5]decane.

The term "aryl" used alone or as part of a larger moiety as in "aralkyl", "aralkoxy", or "aryloxyalkyl", refers to monocyclic and polycyclic ring systems having a total of five to 20 ring members, wherein at least one ring in the system is aromatic and wherein each ring in the system contains three to twelve ring members. The term "aryl" may be used interchangeably with the term "aryl ring". In certain embodiments, "aryl" refers to an aromatic ring system which includes, for example, phenyl, naphthyl, and anthracyl, which may bear one or more substituents. Also included within the scope of the term "aryl", as it is used herein, is a group in which an aromatic ring is fused to one or more additional rings, such as benzofuranyl, indanyl, phthalimidyl, naphthimidyl, phenanthridinyl, and tetrahydronaphthyl.

The terms "heteroaryl" and "heteroar-", used alone or as part of a larger moiety, e.g., "heteroaralkyl", or "heteroaralkoxy", refer to groups having 5 to 14 ring atoms, preferably 5, 6, 9 or 10 ring atoms; having 6, 10, or 14 pi ($\pi$) electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, for example, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, benzofuranyl and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and may be saturated or partially unsaturated, and have, in addition to carbon atoms, one or more, preferably one to four, heteroatoms, as defined above. In some variations, the heterocyclic group is a stable 5- to 7-membered monocyclic or 7- to 14-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, for example, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds described herein may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned herein are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

In some chemical structures herein, substituents are shown attached to a bond which crosses a bond in a ring of the depicted molecule. This means that one or more of the substituents may be attached to the ring at any available position (usually in place of a hydrogen atom of the parent structure). In cases where an atom of a ring so substituted has two substitutable positions, two groups may be present on the same ring atom. When more than one substituent is present, each is defined independently of the others, and each may have a different structure. In cases where the substituent shown crossing a bond of the ring is —R, this has the same meaning as if the ring were said to be "optionally substituted" as described in the preceding paragraph.

Suitable monovalent substituents on a substitutable carbon atom of an "optionally substituted" group are independently halogen; —$(CH_2)_{0-4}R°$; —$(CH_2)_{0-4}OR°$; —O—$(CH_2)_{0-4}C(O)OR°$; —$(CH_2)_{0-4}CH(OR°)_2$; —$(CH_2)_{0-4}SR°$; —$(CH_2)_{0-4}Ph$, which may be substituted with $R°$; —$(CH_2)_{0-4}O(CH_2)_{0-1}Ph$ which may be substituted with $R°$; —CH=CHPh, which may be substituted with $R°$; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)N(R°)_2$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR°$; —$SC(S)SR°$; —$(CH_2)_{0-4}SC(O)R°$; —$(CH_2)_{0-4}C(O)NR°_2$; —$C(S)NR°_2$; —$C(S)SR°$; —$SC(S)SR°$, —$(CH_2)_{0-4}OC(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R°$; —$N(R°)S(O)_2NR°_2$; —$N(R°)S(O)_2R°$; —$N(OR°)R°$; —$C(NH)NR°_2$; —$P(O)_2R°$; —$P(O)R°_2$; —$OP(O)R°_2$; —$OP(O)(OR°)_2$; $SiR°_3$; —($C_{1-4}$ straight or branched alkylene)O—$N(R°)_2$; or —($C_{1-4}$ straight or branched alkylene)C(O)O—$N(R°)_2$, wherein each $R°$ may be substituted as defined below and is independently hydrogen, $C_{1-8}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, and sulfur, or, notwithstanding the definition above, two independent occurrences of $R°$, taken together with their intervening atom(s), form a 3-12-membered saturated, partially unsaturated, or aryl mono- or polycyclic ring having 0-4 heteroatoms independently selected from nitrogen, oxygen, and sulfur, which may be substituted as defined below.

Suitable monovalent substituents on $R°$ (or the ring formed by taking two independent occurrences of $R°$ together with their intervening atoms), are independently halogen, —$(CH_2)_{0-2}R^•$, -(haloR$^•$), —$(CH_2)_{0-2}OH$, —$(CH_2)_{0-2}OR^•$, —$(CH_2)_{0-2}CH(OR^•)_2$; —O(haloR$^•$), —CN, —$N_3$, —$(CH_2)_{0-2}C(O)R^•$, —$(CH_2)_{0-2}C(O)OH$, —$(CH_2)_{0-2}C(O)OR^•$, —$(CH_2)_{0-4}C(O)N(R°)_2$; —$(CH_2)_{0-2}SR^•$, —$(CH_2)_{0-2}SH$, —$(CH_2)_{0-2}NH_2$, —$(CH_2)_{0-2}NHR^•$, —$(CH_2)_{0-2}NR^•_2$, —$NO_2$, —$SiR^•_3$, —$OSiR^•_3$, —$C(O)SR^•$, —$(C_{1-4}$ straight or branched alkylene)$C(O)OR^•$, or —$SSR^•$ wherein each $R^•$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, and sulfur. Suitable divalent substituents on a saturated carbon atom of $R°$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur. Suitable divalent substituents that are bound to vicinal substitutable carbons of an "optionally substituted" group include: —O(CR*$_2$)$_{2-3}$O—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur.

Suitable substituents on the aliphatic group of R* include halogen, —$R^•$, -(haloR$^•$), —OH, —$OR^•$, —O(haloR$^•$), —CN, —C(O)OH, —C(O)OR$^•$, —$NH_2$, —NHR$^•$, —NR$^•_2$, or —$NO_2$, wherein each $R^•$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, and sulfur.

Suitable substituents on a substitutable nitrogen of an "optionally substituted" group include —$R^†$, —$NR^†_2$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†_2$, —C(S)NR$^†_2$, —C(NH)NR$^†_2$, or —N(R$^†$)S(O)$_2$R$^†$; wherein each R$^†$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, and sulfur, or, notwithstanding the definition above, two independent occurrences of R$^†$, taken together with their intervening atom(s) form an unsubstituted 3-12-membered saturated, partially unsaturated, or aryl mono- or bicyclic ring having 0-4 heteroatoms independently selected from nitrogen, oxygen, and sulfur.

Suitable substituents on the aliphatic group of R$^†$ are independently halogen, —R$^•$, -(haloR$^•$), —OH, —OR$^•$, —O(haloR$^•$), —CN, —C(O)OH, —C(O)OR$^•$, —NH$_2$, —NHR$^•$, —NR$^•_2$, or —NO$_2$, wherein each R$^•$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, and sulfur.

As used herein, the term "catalyst" refers to a substance the presence of which increases the rate of a chemical reaction, while not being consumed or undergoing a permanent chemical change itself.

"Tetradentate" refers to ligands having four sites capable of coordinating to a single metal center.

As used herein, the term "about" preceding one or more numerical values means the numerical value ±5%. t should be understood that reference to "about" a value or parameter herein includes (and describes) embodiments that are directed to that value or parameter per se. For example, description referring to "about x" includes description of "x" per se.

DETAILED DESCRIPTION

In certain aspects, provided are integrated processes that enable simultaneous production of valuable chemicals or polymers while upgrading synthesis gas by increasing the hydrogen to carbon monoxide ratio in the gas. The processes described herein represent significant economic and environmental improvements versus prior art methods utilizing the water gas shift reaction which relies on conversion of CO to waste $CO_2$ to increase the hydrogen ratio. The integrated processes herein provide improved carbon efficiency for processes based on coal or biomass gasification or steam methane reforming.

In a first aspect, provided are integrated processes for the conversion of biomass or coal to synthesis gas and commodity chemicals or polymers derived from epoxide carbonylation. In certain embodiments, such methods comprise:
a) in a first reaction zone, contacting syngas derived from gasification of biomass or coal with an epoxide in the presence of a carbonylation catalyst thereby consuming carbon monoxide from the syngas and producing an epoxide carbonylation product,
b) recovering an upgraded gas stream from the first reaction zone wherein the upgraded gas stream has a higher hydrogen to carbon monoxide ratio than the starting syngas stream, and
c) in a second reaction zone, utilizing the upgraded gas stream to conduct a second chemical process requiring a hydrogen to carbon monoxide ratio higher than the ratio in the industrial gas stream utilized in step (a).

A schematic of an exemplary process is shown in FIG. 1. The process begins with a gasifier unit which converts biomass, coal or other carbonaceous feedstocks into a synthesis gas stream 101. Gas stream 101 is directed to carbonylation reactor 200 where it is brought into contact with an epoxide (fed to reactor 200 via stream 201). In reactor 200, the epoxide and carbon monoxide in the syngas stream react in the presence of a carbonylation catalyst to produce epoxide carbonylation products which are ultimately recovered via product stream P1. A hydrogen-enriched syngas stream 102 is recovered from reactor 200 and fed to reactor 300 where it is consumed as the feedstock for Fischer Tropsch synthesis yielding FT products via product stream P2. FIG. 1 also illustrates the prior art process wherein water gas shift reactor 400 is utilized in place of carbonylation reactor 200. In this case, CO in the synthesis gas stream 101 is converted to $CO_2$ and hydrogen in the usual fashion with $CO_2$ exiting via waste stream W1.

In a second aspect, provided are integrated processes for the conversion of methane into hydrogen. In certain embodiments, such methods comprise:
- a) in a first reaction zone, contacting a syngas stream derived from methane steam reforming with an epoxide in the presence of a carbonylation catalyst thereby consuming carbon monoxide from the syngas and producing an epoxide carbonylation product,
- b) recovering an upgraded gas stream from the first reaction zone wherein the upgraded gas stream has a higher hydrogen to carbon monoxide ratio than the starting syngas stream, and
- c) in a second reaction zone, utilizing the upgraded gas stream to conduct a second chemical process requiring a hydrogen to carbon monoxide ratio higher than the ratio in the industrial gas stream utilized in step (a).

Figure 2:
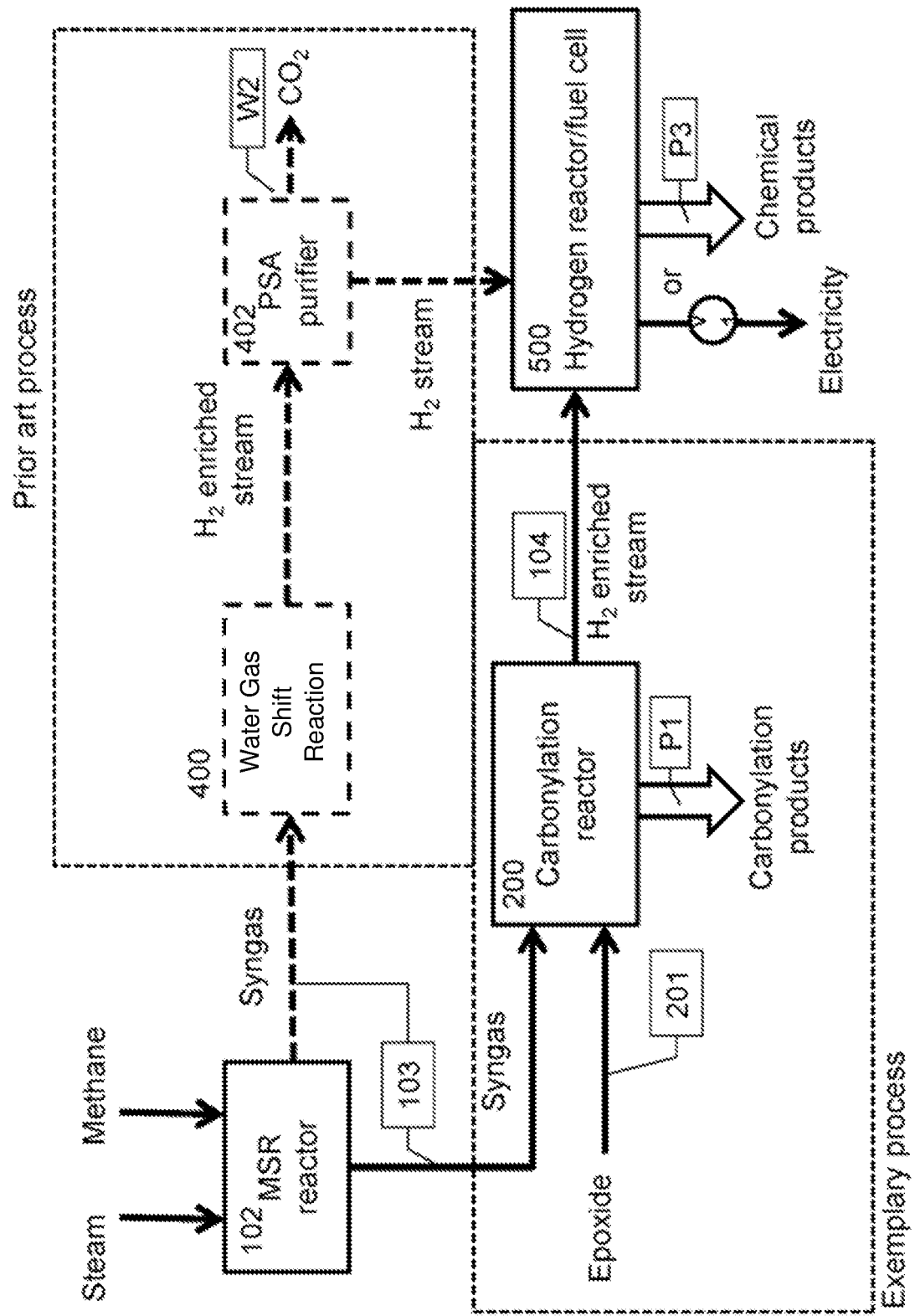
FIG. 2 shows a schematic of an exemplary integrated hydrogen production process.

FIG. 2 shows a schematic of another embodiment of such a process. With reference to FIG. 2, a methane steam reforming reactor 102 which is fed with steam and methane to produce syngas stream 103. Gas stream 103 is fed to carbonylation reactor 200 along with epoxide (via stream 201). The epoxide and carbon monoxide react in the presence of a carbonylation catalyst in reactor 200 to produce product stream P1 containing carbonylation products and a hydrogen-enriched gas stream 104. The hydrogen enriched gas stream 104 can be used for known purposes requiring hydrogen or hydrogen-rich syngas. For example, as shown in FIG. 2, gas stream 104 can optionally be fed to a chemical reactor which consumes hydrogen to make chemical products (e.g. ammonia or hydrogenated products), or to a fuel cell to produce electricity collectively represented by reactor 500 and outputs P3 and V1. As described more fully below, in certain embodiments, carbonylation reactor 200 is operated under conditions such that essentially all of the carbon monoxide in syngas stream 103 is consumed, in which case stream 104 consists of substantially pure hydrogen. These embodiments have the attractive feature of eliminating the need for a pressure swing adsorption unit (e.g. PSA 402) or related purification stages.

In another aspect, provided is an integrated process for the production of hydrogen and commodity chemicals derived from beta lactone carbonylation. In certain embodiments, such methods comprise:
- a) in a first reaction zone, contacting syngas with a beta propiolactone in the presence of a carbonylation catalyst thereby consuming carbon monoxide from the syngas and producing a succinic anhydride product,
- b) recovering an upgraded gas stream from the first reaction zone wherein the upgraded gas stream has a higher hydrogen to carbon monoxide ratio than the starting syngas stream, and
- c) in a second reaction zone, utilizing the upgraded gas stream to conduct a second chemical process requiring a hydrogen to carbon monoxide ratio higher than the ratio in the industrial gas stream utilized in step (a).

Figure 3:
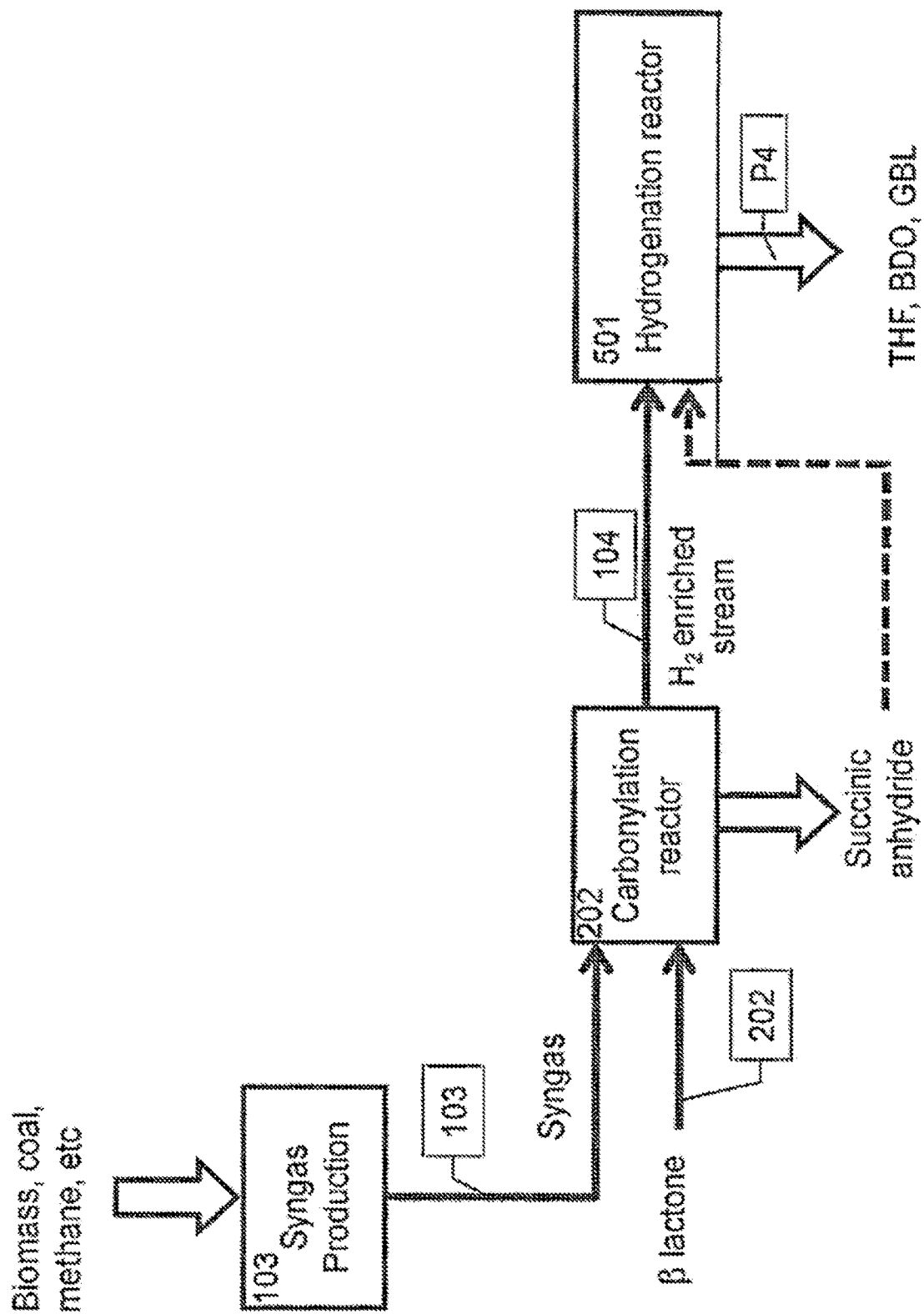
FIG. 3 shows a schematic of an alternate exemplary process production of hydrogen and commodity chemicals derived from beta lactone carbonylation.

FIG. 3 shows a schematic of an exemplary process according to this embodiment. As shown in FIG. 3, Syngas reactor 103 which is fed with appropriate inputs and produces syngas stream 103. Gas stream 103 is fed to carbonylation reactor 200 along with a beta lactone (via stream 202). The lactone and carbon monoxide react in the presence of a carbonylation catalyst in reactor 202 to produce a succinic anhydride product along with gas stream 104 which is enriched in hydrogen relative to stream 103. As shown, the succinic anhydride can optionally be fed to hydrogenation reactor 501 along with the hydrogen stream 104 and contacted under hydrogenation conditions to produce tetrahydrofuran (THF), 1,4 butanediol (BDO), or gamma butyrolactone (GBL).

Figure 4:
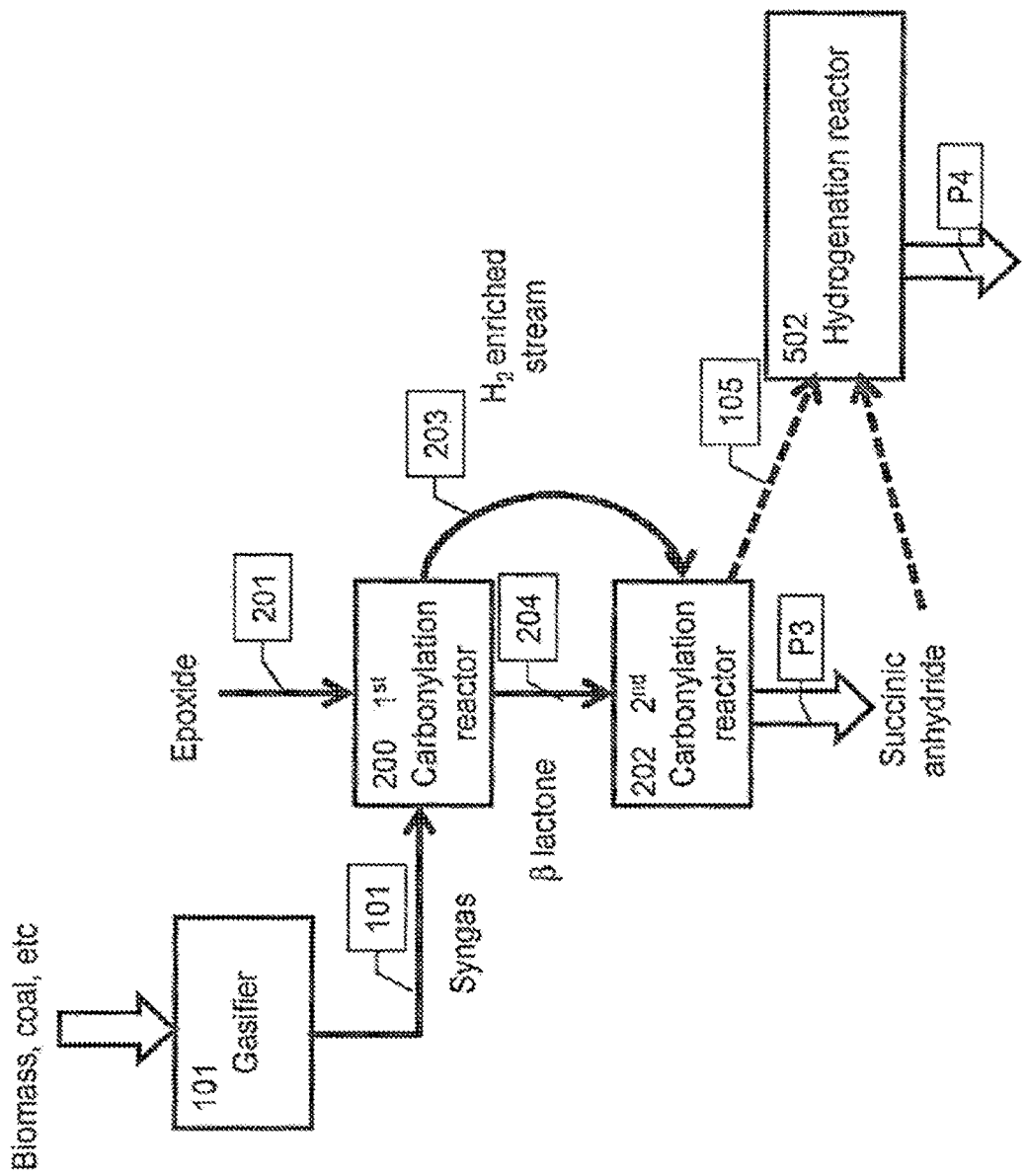
FIG. 4 shows a schematic of an exemplary process utilizing two carbonylation stages.

FIG. 4 shows a schematic of another embodiment where the syngas input is upgraded twice by utilizing two carbonylation stages. As shown in FIG. 4, syngas is produced in gasifier 100 in the usual fashion, the output syngas stream 101 is directed to first carbonylation reactor 200 where it is contacted with an epoxide and a carbonylation catalyst to produce a beta lactone product and hydrogen enriched synthesis gas stream 103. Both the beta lactone and the gas stream 103 are directed to a $2^{nd}$ carbonylation reactor 202 where they are further reacted in the presence of a carbonylation catalyst (which may be the same or different from the catalyst in the $1^{st}$ carbonylation reactor) to produce a succinic anhydride product stream P3 along with a hydrogen stream 105. As shown these streams may optionally be combined in hydrogenation reactor 502 where the anhydride reacts with the hydrogen to produce a product stream P4 containing products selected from the group consisting of THF, BDO and GBL.

Having generally described the spirit of the methods encompassed herein, the following sections provide additional details regarding the compositions of the feedstocks, process streams and products as well as appropriate process conditions and apparatus for practicing the processes described herein.

I) Syngas Production

The methods described herein do not place any specific restrictions on the method by which the syngas input is produced or on the specific composition of the syngas. The terms "synthesis gas" or "syngas" as used herein refer to any gaseous mixture of carbon monoxide and hydrogen. Such mixtures are typically produced from a carbonaceous feedstsock. Syngas production methods include gasification of coal or biomass and steam reforming of methane or other gaseous or liquid hydrocarbons and similar processes.

In certain embodiments, the syngas stream fed to the carbonylation reactor in the methods described herein is characterized in that it has an $H_2$ to CO ratio between about 0.4:1 and about 1.5:1. Such a range is typical for syngas from solids gasification which tends to produce carbon rich syngas. In certain embodiments, the syngas stream fed to the carbonylation reactor is characterized in that it has an $H_2$ to CO ratio of 0.4:1, about 0.5:1, about 0.6:1, about 0.7:1, about 0.8:1, about 1:1, about 1.2:1, about 1.4:1, or about 1.5:1. In certain embodiments, the syngas stream fed to the carbonylation reactor is characterized in that it has an $H_2$ to CO ratio less than about 1.6:1, less than about 1.5:1, less than about 1.3:1, less than about 1.2:1, less than about 1.1:1, less than about 1:1, less than about 0.8:1, less than about 0.7:1, or less than about 0.6:1.

In certain embodiments, the syngas stream fed to the carbonylation reactor in the methods described herein is characterized in that it has an $H_2$ to CO ratio between about 1.5:1 and about 3:1. Such a range is typical for steam reforming processes utilizing methane or other light aliphatic feedstocks. In certain embodiments, the syngas stream fed to the carbonylation reactor is characterized in that it has an $H_2$ to CO ratio of 1.5:1, about 1.6:1, about 1.8:1, about 2:1, about 2.4:1, about 2.8:1, or about 3:1. In certain embodiments, the syngas stream fed to the carbonylation reactor is characterized in that it has an $H_2$ to CO ratio than about 3:1, less than about 2.8:1, less than about 2.5:1, less than about 2.2:1, or less than about 2:1.

Syngas typically contains varying amounts of $CO_2$. In many catalytic processes the $CO_2$ must be removed prior to using the gas. This issue is more acute in processes relying on biomass gasification since the high oxygen content of biobased feedstocks typically produces syngas with high $CO_2$ content (often 20% or more). The presence of $CO_2$ not only potentially compromises downstream catalytic processes, but its presence in the syngas stream means that any process steps (e.g. compression or desulfurization) performed prior to removal of the $CO_2$ are less efficient since the $CO_2$ dilutes the stream and therefore requires higher processing capacity. Unexpectedly, the applicants have discovered that epoxide carbonylation reactions promoted by certain classes of catalysts described below are tolerant of high levels of $CO_2$ in the syngas stream.

Therefore, in certain embodiments, the syngas stream fed to the carbonylation reactor in the methods described herein is characterized in that it contains $CO_2$. In certain embodiments, the syngas stream contains between about 1 mole percent and about 30 mole percent $CO_2$. In certain embodiments, the syngas stream contains between about 1 mole percent and about 5 mole percent $CO_2$, between about 5 mole percent and about 10 mole percent $CO_2$, between about 10 mole percent and about 20 mole percent $CO_2$, or between about 20 mole percent and about 40 mole percent $CO_2$.

Nevertheless, in some circumstances, it may be desirable to provide a syngas stream which contains little or no $CO_2$ to the carbonylation step. Therefore, in certain embodiments, the syngas stream fed to the carbonylation reactor in the methods described herein is characterized in that it contains little or no $CO_2$. In certain embodiments, the syngas stream fed to the carbonylation reactor contains less than about 2000 ppm, less than about 1000 ppm, less than about 500 ppm, less than about 200 ppm, less than about 100 ppm, less than about 50 ppm, less than about 25 ppm, or less than about 10 ppm $CO_2$.

Without being bound by theory or thereby limiting the scope of the claimed invention, it is believed that the presence of sulfur compounds in the syngas stream may be deleterious to the epoxide carbonylation reactions described herein. Therefore, in certain embodiments, the syngas stream fed to the carbonylation reactor is substantially free of sulfur. In certain embodiments, the syngas stream fed to the carbonylation reactor contains less than about 500 ppm, less than 200 ppm, less than about 100 ppm, less than about 50 ppm, less than about 40 ppm, or less than about 25 ppm sulfur. In certain embodiments, the syngas stream fed to the carbonylation reactor contains less than about 10 ppm, less than about 5 ppm, less than about 2 ppm, less than about 1 ppm, or less than about 0.5 ppm sulfur. In certain embodiments, the syngas stream fed to the carbonylation reactor contains less than about 0.2 ppm, less than about 0.1 ppm, less than about 0.05 ppm, less than about 0.01 ppm, or less than about 0.001 ppm sulfur.

It will be appreciated by the skilled artisan that production of syngas is a mature technology which is capable of operating with a diverse array of feedstocks and that numerous process conditions and catalysts for production of syngas are known in the art. Likewise apparatus and methods for the handling and purification of syngas are well known. As such, the selection of appropriate feedstocks and process conditions to produce syngas suitable for practice of the inventive methods described herein will be apparent to the skilled artisan based on the teachings and disclosure herein. The exact choice of feedstocks and processing methods is likely to depend on the local availability of materials and prevailing economic conditions.

II) Carbonylation Reaction Conditions

As described above and in the classes and subclasses herein, the methods described herein comprise contacting the syngas stream with a carbonylation catalyst in the presence of an epoxide or a beta lactone. Catalysts, conditions and processes for these carbonylation reactions are well known in the art and can be employed in the methods described herein.

For embodiments where the syngas is reacted with an epoxide, no particular constraints are placed on the identity of the epoxide. Any epoxide or mixture of epoxides may be used, though as a general principle those epoxides lacking other reactive functional groups (for example protic functional groups) are less desirable since there is an increased likelihood for side reactions with use of such substrates. Also, given the large scale on which syngas production is typically practiced, there is a strong preference to utilize epoxides that are available in bulk as commodity chemicals.

In certain embodiments where the methods entail epoxide carbonylation reactions, the epoxide is selected from the group consisting of: ethylene oxide, propylene oxide, butylene oxide, 1-hexene oxide, epichlorohydrin, and esters or ethers of glycidol. In certain embodiments, the epoxide is selected from the group consisting of ethylene oxide and propylene oxide. In certain embodiments the epoxide is ethylene oxide. In certain embodiments the epoxide is propylene oxide.

The catalytic insertion of CO into epoxides is known to yield several possible products the identity of which is influenced by the particular catalyst utilized and the reaction conditions employed. In certain embodiments, the methods comprise carbonylating an epoxide, and the product of the carbonylation is selected from the group consisting of: a beta lactone, a 3-hydroxy propionic acid, a succinic anhydride (via double carbonylation) and polyesters comprising the alternating copolymer of the epoxide and CO.

In certain embodiments, carbonylation results in the formation of a beta lactone by the general reaction:

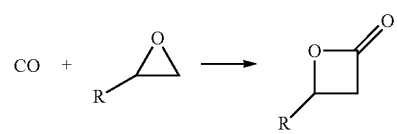

Examples include:
propylene oxide+CO→beta butyrolactone

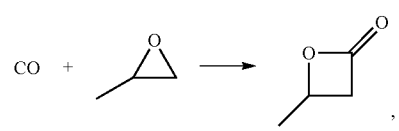

and
ethylene oxide+CO→beta propiolactone

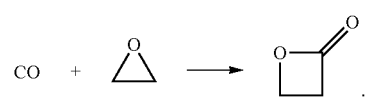

Suitable catalysts and reaction conditions for effecting this reaction are disclosed in published PCT applications:

WO2003/050154, WO2004/089923, WO2012/158573, WO2010/118128, WO2013/063191, and WO2014/008232; in U.S. Pat. Nos. 5,359,081 and 5,310,948 and in the publication "Synthesis of beta-Lactones" J. AM. CHEM. SOC., vol. 124, 2002, pages 1174-1175.

In certain embodiments, carbonylation results in the formation of a polyester by the general reaction:

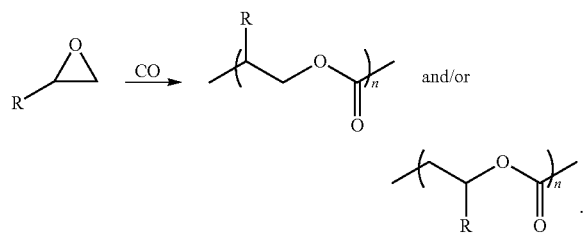

Examples include propylene oxide+CO→poly(3-hydroxybutyrate)

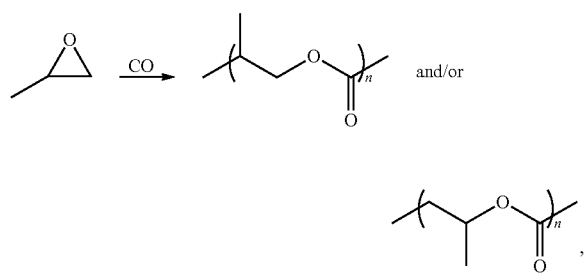

and ethylene oxide+CO→poly propiolactone

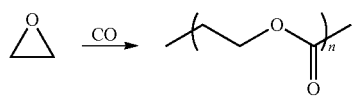

In certain embodiments where methods described herein include carbonylative polymerization, the methods utilize catalysts and/or process conditions disclosed in published PCT applications WO2003/074585A1, WO2011/063309, or WO2014004858.

In certain embodiments, epoxide carbonylation results in the formation of a succinic anhydride by insertion of two molecules of CO. Such processes conform to the general reaction scheme:

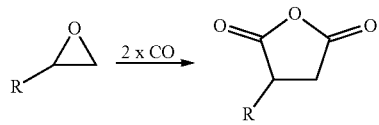

Examples include propylene oxide+CO→methylsuccinic anhydride

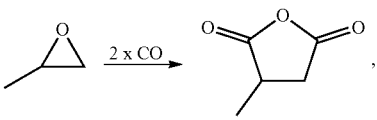

and ethylene oxide+CO→succinic anhydride

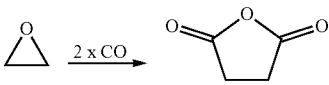

In certain embodiments, where methods described herein include double carbonylation of epoxides, the methods utilize catalysts and/or process conditions disclosed in published PCT applications WO2012/030619 and WO2013/122905, and U.S. Pat. No. 8,481,756.

As described above, certain embodiments of the methods described herein comprise contacting a syngas stream with a beta lactone in the presence of a carbonylation catalyst to yield a succinic anhydride derivative along with a hydrogen-enriched syngas stream. Such processes conform to the general reaction scheme:

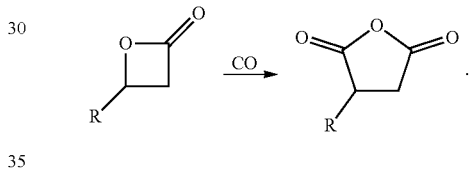

The catalysts and/or process conditions disclosed in published PCT applications WO2012/030619 and WO2013/122905, and U.S. Pat. No. 8,481,756, can be utilized to perform such steps.

In certain embodiments, carbonylation catalysts utilized in the present methods comprise metal carbonyl complexes. In certain embodiments, the catalysts comprise metal carbonyl complexes in combination with one or more other components such as amines, nitrogen-containing heterocycles, Lewis acids, or metal complexes.

In some embodiments, the carbonylation catalyst includes a metal carbonyl compound. Typically, in one variation, a single metal carbonyl compound is provided, but in certain embodiments mixtures of two or more metal carbonyl compounds are provided. (Thus, when a provided metal carbonyl compound "comprises", e.g., a neutral metal carbonyl compound, it is understood that the provided metal carbonyl compound can be a single neutral metal carbonyl compound, or a neutral metal carbonyl compound in combination with one or more additional metal carbonyl compounds.) Preferably, the provided metal carbonyl compound is capable of ring-opening an epoxide and facilitating the insertion of CO into the resulting metal carbon bond. Metal carbonyl compounds with this reactivity are well known in the art and are used for laboratory experimentation as well as in industrial processes such as hydroformylation. Additional description of suitable metal carbonyl compounds is provided herein.

As mentioned above, carbonylation catalysts useful for practicing methods described herein may include one or more additional components in combination with a metal carbonyl compound. In certain embodiments, such additional components comprise organic bases such as optionally substituted amines, guanidines, and amidines. In certain embodiments, such additional components comprise heterocycles such as optionally substituted pyridines, pyrimidines, imidazoles, and the like. In certain embodiments, such additional components comprise neutral Lewis acids such as boranes, aluminum alkyls, $TiCl_4$, $BF_3$, and the like. In certain embodiments, such additional components comprise cationic Lewis acids. Additional description of suitable cationic Lewis acids is provided herein.

In certain embodiments, the carbonylation catalysts employed in methods described herein comprise heterogeneous carbonylation catalysts. In certain embodiments, such heterogeneous catalysts comprise supported metal carbonyl compounds. In certain embodiments, carbonylation catalysts and processes disclosed in WO 2013/063191 may be adapted for use in methods described herein.

The methods described herein provide no specific limitations on the reaction conditions utilized in the carbonylation step. For practical application on industrial scale, the carbonylation reaction will typically be performed in a continuous or semi-continuous format. Where the carbonylation reaction is performed in a continuous fashion, it may be conducted in any suitable reactor format, such as plug flow reactors (PFRs), continuous stirred-tank reactors (CSTRs) or any hybrid or combination of these. Though the carbonylation stage of the methods herein is often described as a single step, it may in fact occur in multiple steps such as within a series of continuous stirred tank reactors or a plug flow reactor fed by one or more CSTRs. Continuous operation requires additional processing steps and suitable apparatus to continuously feed reactants, catalysts, solvents and the like as well as provision to continuously withdraw carbonylation products, recycle the catalyst and solvents, purge impurities, and the like. A detailed description of such processes and apparatus is outside the scope of this disclosure since the requisite knowledge is readily available to the skilled artisan. In certain embodiments, the continuous carbonylation processes described in published PCT applications WO 2010/118128 WO 2012/030619 WO 2013/063191 WO 2013/122905 and WO 2014008232 are suitable for practicing certain embodiments of the methods described herein.

The syngas will typically be fed to the carbonylation reactor at a superatmospheric pressure. No particular limits are placed on the pressure utilized. As with similar processes the chosen operating pressure will require balance of the reaction rate and selectivity at a given pressure with the cost of the equipment required to operate at that pressure. In certain embodiments, the syngas is provided to the carbonylation reactor at a pressure from about 50 psi to about 5,000 psi. If the source of the synthesis gas provides a gas stream at a pressure lower than the desired pressure in the carbonylation step, then the methods will include an additional step of pressurizing the syngas stream prior to contacting it with the epoxide or beta lactone. In certain embodiments, the carbonylation reactor is integrated with a syngas production source that outputs a pressurized source of syngas and the carbonylation reactor is run at a pressure substantially the same as the output from the syngas source.

In certain embodiments, the syngas is provided to the carbonylation reactor at a pressure sufficient to afford a carbon monoxide partial pressure within the reactor from about 0.5 atmospheres to about 350 atmospheres. In certain embodiments, the carbon monoxide partial pressure ranges from about 5 to about 100 atmospheres. In certain embodiments, the carbon monoxide partial pressure ranges from about 10 to about 50 atmospheres, from about 5 to about 20 atmospheres, from about 1 to about 10 atmospheres, or from about 25 to about 50 atmospheres. In some embodiments, carbon monoxide partial pressure within the carbonylation reactor ranges from about 0.5 atmospheres to about 10 atmospheres. In some embodiments, a carbon monoxide partial pressure within the carbonylation reactor ranges from about 0.5 to about 50, from about 1 to about 10, from about 1 to about 50, from about 1 to about 100, from about 10 to about 50, from about 10 to about 100, from about 50 to about 100, from about 50 to about 200, from about 100 to about 200, from about 100 to about 250, from about 200 to about 300, or from about 200 to about 500 atmospheres. In some embodiments, a carbon monoxide partial pressure within the carbonylation reactor is about 10 atmospheres. In some embodiments, a carbon monoxide partial pressure within the carbonylation reactor is about 10, about 20, about 30, about 40, about 50, about 100, about 150, or about 200 atmospheres.

In certain embodiment, the step of contacting the syngas stream with epoxide or beta lactone in the presence of a carbonylation catalyst is performed under conditions such that the hydrogen-to-carbon monoxide ratio in the upgraded syngas stream exiting the reactor is maintained within a specific range. In certain embodiments, the desired range is dependent on the identity of the downstream process in which the upgraded gas stream is to be used. For integrated carbonylation-Fischer Tropsch processes, it is desirable to maintain the $H_2$ to CO ratio of the upgraded syngas stream around 2:1. For integrated carbonylation-hydrogenation processes, it is desirable to maintain the $H_2$ to CO ratio at a high level, or even to consume substantially all of the CO in the syngas feed stream such that the upgraded stream contains little or no CO. Therefore, in certain embodiments, the methods described herein are characterized in that the upgraded syngas stream obtained from the carbonylation reactor has an $H_2$ to CO ratio above about 2:1. In certain embodiments, the upgraded syngas stream obtained from the carbonylation reactor has an $H_2$ to CO ratio above about 2.1:1, above about 2.2:1, above about 2.3:1, above about 2.4:1, above about 2.1:1, above about 2.1:1, above about 2.1:1, above about 2.1:1, above about 2.5:1, above about 2.8:1, above about 3:1, above about 3.5:1, above about 4:1, above about 5:1, or above about 10:1. In certain embodiments, the upgraded syngas stream obtained from the carbonylation reactor has an $H_2$ to CO ratio above about 2.1:1, above about 10:1, above about 20:1, above about 50:1, above about 100:1, above about 200:1, above about 500:1, or above about 1000:1.

In certain embodiments, the methods described herein are characterized in that the upgraded syngas stream obtained from the carbonylation reactor has an $H_2$ to CO ratio of about 2:1. In certain embodiments, the upgraded syngas stream obtained from the carbonylation reactor has an $H_2$ to CO ratio of about 2.1:1, about 2.2:1, about 2.5:1, about 3:1, about 4:1, about 5:1, or about 10:1.

In certain embodiments, the methods described herein are characterized in that the upgraded syngas stream obtained from the carbonylation reactor is essentially free of CO. In certain embodiments, the upgraded syngas stream obtained from the carbonylation reactor contains less than 2%, less than 1%, less than 0.5%, less than 0.2%, or less than 0.1% CO. In certain embodiments, the upgraded syngas stream obtained from the carbonylation reactor contains less than 500 ppm, less than 400 ppm, less than 200 ppm, less than 100 ppm, less than 50 ppm, less than 25 ppm, less than 10 ppm, less than 5 ppm, or less than 1 ppm CO.

III) Utilization of the Upgraded Syngas Stream

The upgraded syngas stream from the carbonylation reactor may be recovered and handled by any suitable means. Typically the upgraded syngas stream will exit the carbonylation reactor via a gas vent, a back-pressure regulator or an outlet port which may include provision for liquids separation, recompression, scrubbing, drying, chilling or heating, and the like as is typically performed in industry. In certain embodiments, the carbonylation reactor is operated at a higher pressure than the downstream process fed with the upgraded syngas stream that exits the carbonylation reactor. This has the advantage of not requiring recompression of the upgraded syngas stream. Nonetheless, this is not always possible if the downstream process is one that requires high hydrogen partial pressures. In this case, the methods described herein will include compressing the upgraded syngas stream prior to utilizing it in next process.

In certain embodiments, the upgraded syngas stream exiting the carbonylation reactor will contain impurities that must be removed prior to utilization of the upgraded stream. For example, if the stream contains carbon dioxide and the downstream process is not tolerant of $CO_2$, then the methods necessarily require an intermediate step to scrub $CO_2$ from the upgraded stream. Such methods are well known in the art and may include membrane separation, pressure swing adsorption, chemical adsorption, cryotreatment and the like. In certain embodiments, volatile residues from the carbonylation reactor may be present in the upgraded syngas stream. Such residues may include solvent, unreacted epoxide, carbonylation side products such as acetaldehyde, volatile metal carbonyl residues and the like. In certain embodiments, the upgraded syngas stream is treated to remove such impurities prior to utilization of the stream in a downstream process. In certain embodiments where the downstream process is tolerant of such residues, it may be preferable to leave the impurities in the upgraded syngas stream and purge them at a later stage in the process.

As described above a feature of some methods described herein is the use of the upgraded syngas stream in a downstream process. Preferably, the carbonylation stage of the methods increases the $H_2$:CO ratio in the stream to a range that is desirable for the downstream process.

In certain embodiments, the downstream process comprises Fischer-Tropsch (FT) synthesis. FT technology is a mature field and appropriate operating conditions, apparatus, catalysts and product isolation techniques for FT processes are well known in the art. The skilled artisan utilizing the wealth of knowledge available in the FT field, together with the teachings herein, will readily apprehend suitable configurations for the FT step described in methods herein. An overview of FT technology is provided in Advance Catalysis, Volume 186, pp 3-12.

In certain embodiments the downstream process in which the upgraded syngas stream is utilized is an FT gas-to-liquid process for the production of fuels and/or chemicals such as olefins and/or alcohols. In certain embodiments, the downstream process in which the upgraded syngas stream is utilized is a Low Temperature FT synthesis (LTFT). In certain embodiments, the downstream process in which the upgraded syngas stream is utilized is a High Temperature FT synthesis (HTFT). The Fischer Tropsch reactor in which the upgraded syngas stream is utilized may be of any known configuration. Suitable configurations include multitubular fixed bed reactors, entrained flow reactors, slurry reactors, bubble reactors, fluidized bed reactors, and riser reactors. Likewise, any known FT catalyst system may be employed in the present methods. Suitable catalysts include, for example, cobalt, iron, ruthenium, nickel, and any combination of two or more of these. The FT catalysts may include additional components as are known in the art including alkali metals, copper, manganese, lanthanide metals or compounds, actinide metals or compounds, alumina, zirconia, and the like.

In certain embodiments, the downstream process in which the upgraded syngas stream is utilized is a process for the production of methane. Suitable catalysts and conditions for methane synthesis from syngas are known in the art and the skilled artisan utilizing the teachings herein with the known art will apprehend suitable conditions, apparatus and catalyst systems to effect the conversion of the upgraded syngas stream to methane.

In certain embodiments, the downstream process in which the upgraded syngas stream is utilized is a process for the production of methanol. Suitable catalysts and conditions for methanol synthesis from syngas are known in the art and the skilled artisan utilizing the teachings herein with the known art will apprehend suitable conditions, apparatus and catalyst systems to effect the conversion of the upgraded syngas stream to methanol.

In certain embodiments the downstream process in which the upgraded syngas stream is utilized is a process for the production of dimethyl ether. Suitable catalysts and conditions for methanol synthesis from syngas are known in the art and the skilled artisan utilizing the teachings herein with the known art will apprehend suitable conditions, apparatus and catalyst systems to effect the conversion of the upgraded syngas stream to methanol.

In other embodiments, the integrated upgraded syngas stream is utilized as a fuel. For example, the upgraded syngas stream can be fed to a fuel cell, combusted in a turbine or boiler, or used to fuel an internal combustion engine. Therefore, depending on the process utilized, processes herein may provide an output comprising steam, thermal energy, electrical energy, or mechanical energy. Due to the higher $H_2$ to CO ratio in the upgraded gas stream, the upgraded stream may have a higher energy content than the starting syngas stream (it will be appreciated that whether or not this is the case will depend on the amount of other gasses such as $CO_2$ that may also be present in the streams).

IV) Integrated Production of FT Products and EO Carbonylation Products

As described above, in certain embodiments, provided are methods for the integrated production of chemicals from syngas derived from gasification.

In certain embodiments, such processes produce as final outputs, beta propiolactone or polypropiolactone (or derivatives of these such as acrylic acid, acrylate esters or superabsorbent polymers) by ethylene oxide carbonylation and FT products such as liquid fuels and related chemicals.

In certain embodiments, methods described herein comprise:
    a) gasifying a carbonaceous solid to provide a syngas stream having an $H_2$ to CO ratio in the range from about 0.4:1 to about 1.2:1;
    b) feeding this syngas stream to an epoxide carbonylation reactor where the syngas stream is contacted with ethylene oxide in the presence of a carbonylation catalyst to deplete the syngas of at least a portion of its CO content and provide a carbonylation product selected from the group consisting of: beta propiolactone, and polypropiolactone;
    c) recovering an upgraded syngas stream from the carbonylation reactor characterized in that the upgraded stream has a higher $H_2$ to CO ratio than the syngas stream provided by step (a); and d) feeding the upgraded syngas stream to a Fischer Tropsch reactor to produce a product selected from the group consisting of: liquid fuels, oils, waxes, olefins, alcohols, and any combination of two or more of these.

In certain embodiments, step (a) of the method above comprises coal gasification. In certain embodiments, such methods are characterized in that the syngas stream in step (a) has an $H_2$ to CO ratio of from about 0.6:1 to about 0.8:1. In certain embodiments, such methods are characterized in that the syngas stream in step (a) has an $H_2$ to CO ratio of about 0.7:1.

In certain embodiments, step (a) of the method above comprises biomass gasification. In certain embodiments, the biomass is selected from the group consisting of: corn stover, sugar cane bagasse, switch grass, municipal solid waste, and wood waste. In certain embodiments, such methods are characterized in that the syngas stream in step (a) has an $H_2$ to CO ratio of from about 0.4:1 to about 0.8:1. In certain embodiments, such methods are characterized in that the syngas stream in step (a) has an $H_2$ to CO ratio of about 0.6:1. In certain embodiments, such methods are characterized in that the syngas stream in step (a) has an $H_2$ to CO ratio of about 0.5:1.

In certain embodiments, the method above further comprises compressing the syngas stream prior to feeding it to the carbonylation reactor. In certain embodiments, the method above further comprises removing sulfurous compounds from the syngas stream prior to feeding it to the carbonylation reactor. In certain embodiments, the method above further comprises drying the syngas stream prior to feeding it to the carbonylation reactor. In certain embodiments, the method above further comprises removing $CO_2$ from the syngas stream prior to feeding it to the carbonylation reactor. In certain embodiments, the method above is characterized in that $CO_2$ is not removed from the syngas stream prior to feeding it to the carbonylation reactor.

In certain embodiments, the product of step (b) of the method above comprises beta propiolactone and the method further comprises converting the beta propiolactone to acrylic acid, or acrylate esters.

In certain embodiments, the product of step (b) of the method above comprises beta propiolactone and the method further comprises converting the beta propiolactone to succinic anhydride. In certain embodiments such methods comprise an additional step of converting the succinic anhydride to a product selected from the group consisting of: succinic acid, 1,4 butanediol, tetrahydrofuran, gamma butyrolactone, or any combination of two or more of these.

In certain embodiments where the method above further comprises converting beta propiolactone to succinic anhydride, the conversion is conducted in a second carbonylation reactor. In certain embodiments, the second carbonylation reactor is also fed with the syngas stream produced in step (a) where it is contacted with the beta propiolactone in the presence of a carbonylation catalyst to deplete the syngas of at least a portion of its CO content and provide succinic anhydride as a second carbonylation product. In certain embodiments, a second upgraded syngas stream, characterized in that it has a higher $H_2$ to CO ratio that the syngas stream produced in step (a) is recovered from the second carbonylation reactor. In certain embodiments, the first and second upgraded syngas streams are combined and utilized in step (d).

In certain embodiments where the method above further comprises converting beta propiolactone to succinic anhydride, the conversion is conducted in a second carbonylation reactor which is fed with the upgraded syngas stream produced in step (b) where it is contacted with the beta propiolactone in the presence of a carbonylation catalyst to further deplete the upgraded syngas stream of its CO thereby providing a twice-upgraded syngas stream having a higher $H_2$ to CO ratio than the upgraded syngas stream from step (c). In certain embodiments, the method comprises an additional step of recovering the twice upgraded syngas stream from the second carbonylation reactor and feeding it to the FT reactor in step (d).

In certain embodiments, the product of step (b) of the method above comprises polypropiolactone and the method further comprises pyrolyzing the polypropiolactone to produce acrylic acid.

In certain embodiments, the carbonylation catalyst in step (b) of the method above comprises a metal carbonyl compound. In certain embodiments, the metal carbonyl compound is selected from any of those described herein. In certain embodiments, the metal carbonyl compound comprises a cobalt carbonyl compound. In certain embodiments, metal carbonyl compound comprises a rhodium carbonyl compound. In certain embodiments, the carbonylation catalyst in step (b) of the method above comprises a metal carbonyl compound in combination with another component selected from the group consisting of: organic bases, neutral Lewis acids, and cationic Lewis acids. In certain embodiments, the carbonylation catalyst in step (b) of the method above comprises an anionic cobalt carbonyl compound in combination with a cationic Lewis acid. In certain embodiments, such cationic Lewis acids comprise metal ligand complexes. In certain embodiments, the metal ligand complexes comprise any complex described herein. In certain embodiments, such metal ligand complexes comprise a metal atom coordinated to a multidentate ligand. In certain embodiments, such metal ligand complexes comprise an aluminum or chromium atom. In certain embodiments, such metal ligand complexes comprise a porphyrin or salen ligand. In certain embodiments, the carbonylation catalyst in step (b) of the method above comprises any combination of a metal carbonyl compound and a metal complex, as described herein.

In certain embodiments, step (c) in the method above is characterized in that the upgraded syngas stream recovered has an $H_2$ to CO ratio between about 1.2:1 and about 3:1. In certain embodiments, the upgraded syngas stream recovered has an $H_2$ to CO ratio between about 1.6:1 and about 2.8:1, between about 1.8:1 and about 2.6:1, between about 1.8:1 and about 2.2:1, or between about 1.9:1 and about 2.1:1. In certain embodiments, the upgraded syngas stream recovered has an $H_2$ to CO ratio of about 2:1.

In certain embodiments, the method above is characterized in that the reaction pressure in the carbonylation reactor is higher than the reaction pressure in the FT reactor. In certain embodiments, the upgraded syngas stream is fed to the FT reactor without an intermediate compression step. In certain embodiments, the upgraded syngas stream exits the carbonylation reactor via a backpressure regulator and is fed directly to the FT reactor.

In certain embodiments, the method above is characterized in that the upgraded syngas stream is treated to remove one or more components prior to feeding the stream to the FT reactor. In certain embodiments, the upgraded syngas stream is treated to remove residual solvent prior to feeding the stream to the FT reactor. In certain embodiments, the upgraded syngas stream is treated to remove residual epoxide prior to feeding the stream to the FT reactor. In certain embodiments, the upgraded syngas stream is treated to remove carbon dioxide prior to feeding the stream to the FT reactor.

In certain embodiments, the method above is characterized in that the FT reactor in step (d) is a Low Temperature FT synthesis (LTFT) reactor. In certain embodiments, the downstream process in which the upgraded syngas stream is utilized is a High Temperature FT synthesis (HTFT) reactor.

In certain embodiments, the method above is characterized in that the overall process has a carbon efficiency greater than 50%. That is, at least 50% of the carbon atoms fed to the gasification reactor are contained in the combined products from the EO carbonylation reactor and the FT reactor. In certain embodiments, the method is characterized in that the overall process has a carbon efficiency greater than 55%, greater than 60%, greater than 62%, greater than 63%, greater than 64%, or greater than 65%. In certain embodiments, the method is characterized in that the overall process has a carbon efficiency greater than 66%, greater than 67%, greater than 68%, greater than 69%, or greater than 70%. In certain embodiments, the method is characterized in that the overall process has a carbon efficiency between about 50% and about 60%. In certain embodiments, the method is characterized in that the overall process has a carbon efficiency between about 55% and about 60%. In certain embodiments, the method is characterized in that the overall process has a carbon efficiency between about 60% and about 64%. In certain embodiments, the method is characterized in that the overall process has a carbon efficiency between about 64% and about 67%. In certain embodiments, the method is characterized in that the overall process has a carbon efficiency between about 67% and about 70%.

In certain embodiments, the method above is characterized in that the FT process in step (d) is fed with syngas from the gasification process in step (a) without utilizing the water gas shift reaction to increase its $H_2$ to CO ratio.

V) Integrated Production of Hydrogen and EO Carbonylation Products

As described above, in certain embodiments, provided are methods for the integrated production of chemicals and hydrogen.

In certain embodiments, such processes produce as final outputs, beta propiolactone or polypropiolactone (or derivatives of these such as acrylic acid, acrylate esters or superabsorbent polymers) by ethylene oxide carbonylation and hydrogen or products of hydrogen such as electrical energy, ammonia, or hydrogenated chemicals.

In certain embodiments, the methods comprise:
a) producing a syngas stream by steam reforming of methane or other lower aliphatic compounds;
b) feeding this syngas stream to an epoxide carbonylation reactor where the syngas stream is contacted with ethylene oxide in the presence of a carbonylation catalyst to deplete the syngas of at least a portion of its CO content and provide a carbonylation product selected from the group consisting of: beta propiolactone, and polypropiolactone; and
c) recovering a hydrogen stream from the carbonylation reactor characterized in that the hydrogen stream has a higher $H_2$ to CO ratio than the syngas stream provided by step (a).

In certain embodiments, step (a) of the method above comprises steam methane reforming. In certain embodiments, such methods are characterized in that the syngas stream in step (a) has an $H_2$ to CO ratio of from about 2.8:1 to about 3.2:1. In certain embodiments, such methods are characterized in that the syngas stream in step (a) has an $H_2$ to CO ratio of about 3:1.

In certain embodiments, the method above further comprises compressing the syngas stream prior to feeding it to the carbonylation reactor. In certain embodiments, the method above further comprises removing sulfurous compounds from the syngas stream prior to feeding it to the carbonylation reactor. In certain embodiments, the method above further comprises drying the syngas stream prior to feeding it to the carbonylation reactor. In certain embodiments, the method above further comprises removing $CO_2$ from the syngas stream prior to feeding it to the carbonylation reactor. In certain embodiments, the method above is characterized in that $CO_2$ is not removed from the syngas stream prior to feeding it to the carbonylation reactor.

In certain embodiments, the product of step (b) of the method above comprises beta propiolactone and the method comprises an additional step of converting the beta propiolactone to acrylic acid, or acrylate esters.

In certain embodiments, the product of step (b) of the method above comprises polypropiolactone and the method further comprises pyrolyzing the polypropiolactone to produce acrylic acid.

In certain embodiments, the carbonylation catalyst in step (b) of the method above comprises a metal carbonyl compound. In certain embodiments, the metal carbonyl compound is selected from any of those described herein. In certain embodiments, the metal carbonyl compound comprises a cobalt carbonyl compound. In certain embodiments, metal carbonyl compound comprises a rhodium carbonyl compound. In certain embodiments, the carbonylation catalyst in step (b) of the method above comprises a metal carbonyl compound in combination with another component selected from the group consisting of: organic bases, neutral Lewis acids, and cationic Lewis acids. In certain embodiments, the carbonylation catalyst in step (b) of the method above comprises an anionic cobalt carbonyl compound in combination with a cationic Lewis acid. In certain embodiments, such cationic Lewis acids comprise metal ligand complexes. In certain embodiments, the metal ligand complexes comprise any complex described herein. In certain embodiments, such metal ligand complexes comprise a metal atom coordinated to a multidentate ligand. In certain embodiments, such metal ligand complexes comprise an aluminum or chromium atom. In certain embodiments, such metal ligand complexes comprise a porphyrin or salen ligand. In certain embodiments, the carbonylation catalyst in step (b) of the method above comprises any combination of a metal carbonyl compound and a metal complex, as described herein.

In certain embodiments, the method above is characterized in that the hydrogen stream recovered in step (c) has an $H_2$ to CO ratio between about 4:1 and about 1,000:1. In certain embodiments, the upgraded syngas stream recovered has an $H_2$ to CO ratio between about 5:1 and about 10:1, between about 10:1 and about 50:1, between about 50:1 and about 100:1, or between about 100:1 and about 1000:1. In certain embodiments, the hydrogen stream contains essentially no CO.

In certain embodiments, the method above is characterized in that the hydrogen stream is treated to remove one or more components prior to use. In certain embodiments, the hydrogen stream is treated to remove residual solvent prior to use. In certain embodiments, the hydrogen stream is treated to remove residual epoxide prior to use. In certain embodiments, the hydrogen stream is treated to remove carbon dioxide prior to use.

In certain embodiments, the method above is characterized in that the hydrogen stream is utilized on site for a process selected from: ammonia synthesis, powering a fuel cell, hydrogenation, and any combination of two or more of these. In certain embodiments, the hydrogen is compressed and distributed for use elsewhere.

In certain embodiments, the method above is characterized in that the overall process has a carbon efficiency greater than 50%. That is, at least 50% of the carbon atoms fed to the steam reforming reactor are contained in products from the EO carbonylation reactor. In certain embodiments, the method is characterized in that the overall process has a carbon efficiency greater than 55%, greater than 60%, greater than 62%, greater than 63%, greater than 64%, or greater than 65%. In certain embodiments, the method is characterized in that the overall process has a carbon efficiency greater than 66%, greater than 67%, greater than 68%, greater than 69%, or greater than 70%. In certain embodiments, the method is characterized in that the overall process has a carbon efficiency between about 50% and about 60%. In certain embodiments, the method is characterized in that the overall process has a carbon efficiency between about 55% and about 60%. In certain embodiments, the method is characterized in that the overall process has a carbon efficiency between about 60% and about 64%. In certain embodiments, the method is characterized in that the overall process has a carbon efficiency between about 64% and about 67%. In certain embodiments, the method is characterized in that the overall process has a carbon efficiency between about 67% and about 70%.

VI) Integrated Production of Hydrogen and C4 Chemical Products

In certain embodiments, provided are methods for the integrated production of C4 chemicals and hydrogen.

In certain embodiments, such processes produce as final outputs, succinic anhydride (or derivatives of succinic anhydride such as succinic acid, 1,4-butanediol, THF and gamma butyrolactone) and hydrogen or products of hydrogen such as electrical energy, ammonia, or hydrogenated chemicals.

In certain embodiments, the methods comprise:
a) producing a syngas stream by steam reforming of methane or other lower aliphatic compounds;
b) feeding this syngas stream to a carbonylation reactor where the syngas stream is contacted with a substrate selected from ethylene oxide, beta propiolactone and combinations of these, in the presence of a carbonylation catalyst to deplete the syngas of at least a portion of its CO content and provide succinic anhydride as a carbonylation product; and
c) recovering a hydrogen stream from the carbonylation reactor characterized in that the hydrogen stream has a higher $H_2$ to CO ratio than the syngas stream provided by step (a).

In certain embodiments, step (a) of the method above comprises steam methane reforming. In certain embodiments, such methods are characterized in that the syngas stream in step (a) has an $H_2$ to CO ratio of from about 2.8:1 to about 3.2:1. In certain embodiments, such methods are characterized in that the syngas stream in step (a) has an $H_2$ to CO ratio of about 3:1.

In certain embodiments, the method above further comprises compressing the syngas stream prior to feeding it to the carbonylation reactor. In certain embodiments, the method above further comprises removing sulfurous compounds from the syngas stream prior to feeding it to the carbonylation reactor. In certain embodiments, the method above further comprises drying the syngas stream prior to feeding it to the carbonylation reactor. In certain embodiments, the method above further comprises removing $CO_2$ from the syngas stream prior to feeding it to the carbonylation reactor. In certain embodiments, the method above is characterized in that $CO_2$ is not removed from the syngas stream prior to feeding it to the carbonylation reactor.

In certain embodiments, step (b) of the method above comprises double carbonylation of ethylene oxide to produce the succinic anhydride. In certain embodiments, the double carbonylation proceeds in the presence of a single carbonylation catalyst, while in other embodiments, the double carbonylation proceeds with the aid of two or more separate catalysts.

In certain embodiments, the double carbonylation of ethylene oxide occurs in a single reactor, while in other embodiments, the two carbonylation steps occur in the two or more reactors. The utilization of two reactors is advantageous in certain embodiments, because of the kinetics of the two carbonylation steps. Without being bound by theory or thereby limiting the scope of the present invention, it is believed that carbonylation of ethylene oxide to produce beta lactones may be zero order in epoxide concentration (e.g., the rate of EO conversion is independent of EO concentration. Therefore, it is believed that a continuous EO carbonylation reactor can be operated efficiently under steady state conditions and maintain a low concentration of EO in the product stream. Conversely, it is believed that the carbonylation of beta lactones is not zero order in lactone and the reaction rate is sensitive to lactone concentration. Therefore, to achieve high conversion in carbonylation of lactones it is believed this step is best performed under plug flow conditions so that a significant proportion of the lactone is consumed. Therefore, in certain embodiments of the method described above, the conversion of ethylene oxide to succinic anhydride occurs in two or more reactors. In certain embodiments, the reactors are operated under different conditions to maximize the efficiency of each of the two carbonylation steps. In certain embodiments ethylene oxide is contacted with the syngas stream in a first carbonylation reactor to provide beta propiolactone as an intermediate product which is fed to a second carbonylation reactor where it is converted to succinic anhydride. In certain embodiments of such methods, the first carbonylation reactor is a steady state reactor. In certain embodiments, the second reactor is a plug flow reactor. In certain embodiments of such methods, the first carbonylation reactor is a steady state reactor and the second reactor is a plug flow reactor. In certain embodiments, the second carbonylation reactor is fed with an upgraded syngas stream recovered from the first carbonylation reactor where the upgraded syngas stream has a higher $H_2$ to CO ratio than the syngas stream produced in step (a).

In other embodiments where the carbonylation occurs in two or more reactors, each of two carbonylation reactors is fed with the syngas stream from step (a). In certain embodiments, a hydrogen stream is obtained from each of the carbonylation reactors. In certain embodiments where multiple hydrogen streams are obtained from two or more reactors, they are combined. In other embodiments, each of the streams is used separately.

In certain embodiments, the carbonylation catalyst in step (b) of the method above comprises a metal carbonyl compound. In certain embodiments, the metal carbonyl compound is selected from any of those described herein. In certain embodiments, the metal carbonyl compound comprises a cobalt carbonyl compound. In certain embodiments, metal carbonyl compound comprises a rhodium carbonyl compound. In certain embodiments, the carbonylation catalyst in step (b) of the method above comprises a metal carbonyl compound in combination with another component selected from the group consisting of: organic bases, neutral Lewis acids, and cationic Lewis acids. In certain embodiments, the carbonylation catalyst in step (b) of the method above comprises an anionic cobalt carbonyl compound in combination with a cationic Lewis acid. In certain embodiments, such cationic Lewis acids comprise metal ligand complexes. In certain embodiments, the metal ligand complexes comprise any complex described herein. In certain embodiments, such metal ligand complexes comprise a metal atom coordinated to a multidentate ligand. In certain embodiments, such metal ligand complexes comprise an aluminum or chromium atom. In certain embodiments, such metal ligand complexes comprise a porphyrin or salen ligand. In certain embodiments, the carbonylation catalyst in step (b) of the method above comprises any combination of a metal carbonyl compound and a metal complexes described herein.

In certain embodiments, the method above is characterized in that the hydrogen stream recovered in step (c) has an $H_2$ to CO ratio between about 4:1 and about 1,000:1. In certain embodiments, the upgraded syngas stream recovered has an $H_2$ to CO ratio between about 5:1 and about 10:1, between about 10:1 and about 50:1, between about 50:1 and about 100:1, or between about 100:1 and about 1000:1. In certain embodiments, the hydrogen stream contains essentially no CO.

In certain embodiments, the method above is characterized in that the hydrogen stream is treated to remove one or more components prior to use. In certain embodiments, the hydrogen stream is treated to remove residual solvent prior to use. In certain embodiments, the hydrogen stream is treated to remove residual epoxide prior to use. In certain embodiments, the hydrogen stream is treated to remove carbon dioxide prior to use.

In certain embodiments, the method above is characterized in that the hydrogen stream is utilized on site for a process selected from: ammonia synthesis, powering a fuel cell, hydrogenation, and any combination of two or more of these. In certain embodiments, the hydrogen is compressed and distributed for use elsewhere.

In certain embodiments, the hydrogen stream is utilized for hydrogenation of the succinic anhydride produced in step (b). In certain embodiments, the hydrogenation of succinic anhydride from step (b) with the hydrogen stream from step (c) produces 1,4-butanediol. In certain embodiments, the hydrogenation of succinic anhydride from step (b) with the hydrogen stream from step (c) produces THF. In certain embodiments, the hydrogenation of succinic anhydride from step (b) with the hydrogen stream from step (c) produces gamma butyrolactone. Methods and catalysts for conversion of maleic and succinic anhydride or their corresponding acids to the products 1,4-BDO, THF and GBL are known in the art and can be adapted by the skilled artisan to serve in the present methods.

In certain embodiments, the method above is characterized in that the overall process has a carbon efficiency greater than 50%. That is, at least 50% of the carbon atoms fed to the steam reforming reactor are contained in products from the EO carbonylation reactor. In certain embodiments, the method is characterized in that the overall process has a carbon efficiency greater than 55%, greater than 60%, greater than 62%, greater than 63%, greater than 64%, or greater than 65%. In certain embodiments, the method is characterized in that the overall process has a carbon efficiency greater than 66%, greater than 67%, greater than 68%, greater than 69%, or greater than 70%. In certain embodiments, the method is characterized in that the overall process has a carbon efficiency between about 50% and about 60%. In certain embodiments, the method is characterized in that the overall process has a carbon efficiency between about 55% and about 60%. In certain embodiments, the method is characterized in that the overall process has a carbon efficiency between about 60% and about 64%. In certain embodiments, the method is characterized in that the overall process has a carbon efficiency between about 64% and about 67%. In certain embodiments, the method is characterized in that the overall process has a carbon efficiency between about 67% and about 70%.

In certain embodiments, step (b) of the method above comprises two substeps. In a first substep, the syngas stream from step (a) is contacted with ethylene oxide to provide beta propiolactone along with an upgraded syngas stream having a higher $H_2$ to CO ratio than the syngas stream from step (a) and, in a second substep, the beta propiolactone is directed to a second carbonylation reactor where it is contacted with the upgraded syngas stream in the presence of a carbonylation catalyst (which may be the same as or different from the carbonylation catalyst utilized in the first substep) to convert the beta propiolactone to succinic anhydride. In certain embodiments such methods further comprise converting the succinic anhydride to a product selected from the group consisting of: succinic acid, 1,4 butanediol, tetrahydrofuran, gamma butyrolactone, or any combination of two or more of these.

In certain embodiments where the method above further comprises converting beta propiolactone to succinic anhydride, the conversion is conducted in a second carbonylation reactor. In certain embodiments, the second carbonylation reactor is fed with the upgraded syngas stream produced in step (b) where the upgraded syngas is contacted with the beta propiolactone in the presence of a carbonylation catalyst to further deplete the upgraded syngas stream of its CO thereby providing a twice-upgraded syngas stream having a higher $H_2$ to CO ratio than the upgraded syngas stream from step (c).

VII) Integrated Production of Methanol and EO Carbonylation Products

As described above, in certain embodiments, provided are methods for the integrated production of methanol from syngas derived from gasification.

In certain embodiments, such processes produce as final outputs, beta propiolactone or polypropiolactone (or derivatives of these such as acrylic acid, acrylate esters or superabsorbent polymers) by ethylene oxide carbonylation and methanol or methanol-derived products such dimethyl ether or olefins via a methanol-to-olefins process (MTO).

In certain embodiments, the methods comprise:
a) treating a carbon-based feedstock to provide a syngas stream having a $H_2$ to CO ratio less than 2:1;
b) feeding this syngas stream to an epoxide carbonylation reactor where the syngas stream is contacted with ethylene oxide in the presence of a carbonylation catalyst to deplete the syngas of at least a portion of its CO content and provide a carbonylation product selected from the group consisting of: beta propiolactone, polypropiolactone and succinic anhydride;
c) recovering an upgraded syngas stream from the carbonylation reactor characterized in that the upgraded stream has a higher $H_2$ to CO ratio than the syngas stream provided by step (a); and d) feeding the upgraded syngas stream to a methanol synthesis reactor.

In certain embodiments, step (a) of the method above comprises coal gasification. In certain embodiments, such methods are characterized in that the syngas stream in step (a) has an $H_2$ to CO ratio of from about 0.6:1 to about 0.8:1. In certain embodiments, such methods are characterized in that the syngas stream in step (a) has an $H_2$ to CO ratio of about 0.7:1.

In certain embodiments, step (a) of the method above comprises biomass gasification. In certain embodiments, the biomass is selected from the group consisting of: corn stover, sugar cane bagasse, switch grass, municipal solid waste, and wood waste. In certain embodiments, such methods are characterized in that the syngas stream in step (a) has an $H_2$ to CO ratio of from about 0.4:1 to about 0.8:1. In certain embodiments, such methods are characterized in that the syngas stream in step (a) has an $H_2$ to CO ratio of about 0.6:1. In certain embodiments, such methods are characterized in that the syngas stream in step (a) has an $H_2$ to CO ratio of about 0.5:1.

In certain embodiments, the method above further comprises compressing the syngas stream prior to feeding it to the carbonylation reactor. In certain embodiments, the method above further comprises removing sulfurous compounds from the syngas stream prior to feeding it to the carbonylation reactor. In certain embodiments, the method above further comprises drying the syngas stream prior to feeding it to the carbonylation reactor. In certain embodiments, the method above further comprises removing $CO_2$ from the syngas stream prior to feeding it to the carbonylation reactor. In certain embodiments, the method above is characterized in that $CO_2$ is not removed from the syngas stream prior to feeding it to the carbonylation reactor.

In certain embodiments, the product of step (b) of the method above comprises beta propiolactone and the method further comprises converting the beta propiolactone to acrylic acid, or acrylate esters.

In certain embodiments, the product of step (b) of the method above comprises beta propiolactone and the method further comprises converting the beta propiolactone to succinic anhydride. In certain embodiments such methods comprise an additional step of converting the succinic anhydride to a product selected from the group consisting of: succinic acid, 1,4 butanediol, tetrahydrofuran, gamma butyrolactone, or any combination of two or more of these.

In certain embodiments where the method above further comprises converting beta propiolactone to succinic anhydride, the conversion is conducted in a second carbonylation reactor. In certain embodiments, the second carbonylation reactor is also fed with the syngas stream produced in step (a) where it is contacted with the beta propiolactone in the presence of a carbonylation catalyst to deplete the syngas of at least a portion of its CO content and provide succinic anhydride as a second carbonylation product. In certain embodiments, a second upgraded syngas stream, characterized in that it has a higher $H_2$ to CO ratio that the syngas stream produced in step (a) is recovered from the second carbonylation reactor. In certain embodiments, the first and second upgraded syngas streams are combined and utilized in step (d).

In certain embodiments where the method above further comprises converting beta propiolactone to succinic anhydride, the conversion is conducted in a second carbonylation reactor which is fed with the upgraded syngas stream produced in step (b) where it is contacted with the beta propiolactone in the presence of a carbonylation catalyst to further deplete the upgraded syngas stream of its CO thereby providing a twice-upgraded syngas stream having a higher $H_2$ to CO ratio than the upgraded syngas stream from step (c). In certain embodiments, the method further comprises recovering the twice upgraded syngas stream from the second carbonylation reactor and feeding it to the methanol reactor in step (d).

It should generally be understood that reference to "a first reaction zone" and "a second reaction zone", etc. or "a first reactor" and "a second reactor", etc., or "a first stream" and "a second stream", etc., does not necessarily imply an order of the reaction zones, reactors or streams. In some variations, the use of such references denotes the number of reaction zones, reactors or streams present. In other variations, an order may be implied by the context in which the reaction zones, reactors or streams are configured or used.

In certain embodiments, the product of step (b) of the method above is polypropiolactone and the method further comprises pyrolyzing the polypropiolactone to produce acrylic acid.

In certain embodiments, the carbonylation catalyst in step (b) of the method above comprises a metal carbonyl compound. In certain embodiments, the metal carbonyl compound is selected from any of those described herein. In certain embodiments, the metal carbonyl compound comprises a cobalt carbonyl compound. In certain embodiments, metal carbonyl compound comprises a rhodium carbonyl compound. In certain embodiments, the carbonylation catalyst in step (b) of the method above comprises a metal carbonyl compound in combination with another component selected from the group consisting of: organic bases, neutral Lewis acids, and cationic Lewis acids. In certain embodiments, the carbonylation catalyst in step (b) of the method above comprises an anionic cobalt carbonyl compound in combination with a cationic Lewis acid. In certain embodiments, such cationic Lewis acids comprise metal ligand complexes. In certain embodiments, the metal ligand complexes comprise any complex described herein. In certain embodiments, such metal ligand complexes comprise a metal atom coordinated to a multidentate ligand. In certain embodiments, such metal ligand complexes comprise an aluminum or chromium atom. In certain embodiments, such metal ligand complexes comprise a porphyrin or salen ligand. In certain embodiments, the carbonylation catalyst in step (b) of the method above comprises any combination of a metal carbonyl compound and a metal complex, as described herein.

In certain embodiments, step (c) in the method above is characterized in that the upgraded syngas stream recovered has an $H_2$ to CO ratio between about 1.2:1 and about 3:1. In certain embodiments, the upgraded syngas stream recovered has an $H_2$ to CO ratio between about 1.6:1 and about 2.8:1, between about 1.8:1 and about 2.6:1, between about 1.8:1 and about 2.2:1, or between about 1.9:1 and about 2.1:1. In certain embodiments, the upgraded syngas stream recovered has an $H_2$ to CO ratio of about 2:1.

In certain embodiments, the method above is characterized in that the reaction pressure in the carbonylation reactor is higher than the reaction pressure in the methanol synthesis reactor. In certain embodiments, the upgraded syngas stream is fed to the methanol synthesis reactor without an intermediate compression step. In certain embodiments, the upgraded syngas stream exits the carbonylation reactor via a backpressure regulator and is fed directly to the methanol synthesis reactor.

In certain embodiments, the method above is characterized in that the upgraded syngas stream is treated to remove one or more components prior to use in the methanol synthesis step. In certain embodiments, the upgraded syngas stream is treated to remove residual solvent prior to feeding the stream to the methanol synthesis reactor. In certain embodiments, the upgraded syngas stream is treated to remove residual epoxide prior to feeding the stream to the methanol synthesis reactor. In certain embodiments, the upgraded syngas stream is treated to remove carbon dioxide prior to feeding the stream to the methanol synthesis reactor.

In certain embodiments, the method above is characterized in that the methanol synthesis reactor in step (d) utilizes a catalyst comprising one or more of, copper, alumina and zinc oxide.

In certain embodiments, the method above further comprises feeding methanol produced in the methanol reactor to an MTO reactor where it is converted to olefins. In certain embodiments, the MTO reactor converts the methanol to ethylene, propylene or a mixture of ethylene and propylene.

In embodiments where the process is integrated to an MTO reactor, the possibility exists for a process that produces carbonylation products derived entirely from the carbon source fed to the syngas production step. This is achieved by utilizing ethylene or propylene from the MTO stage to produce ethylene oxide or propylene oxide which is then utilized as the feedstock for the carbonylation reactor.

Figure 5:
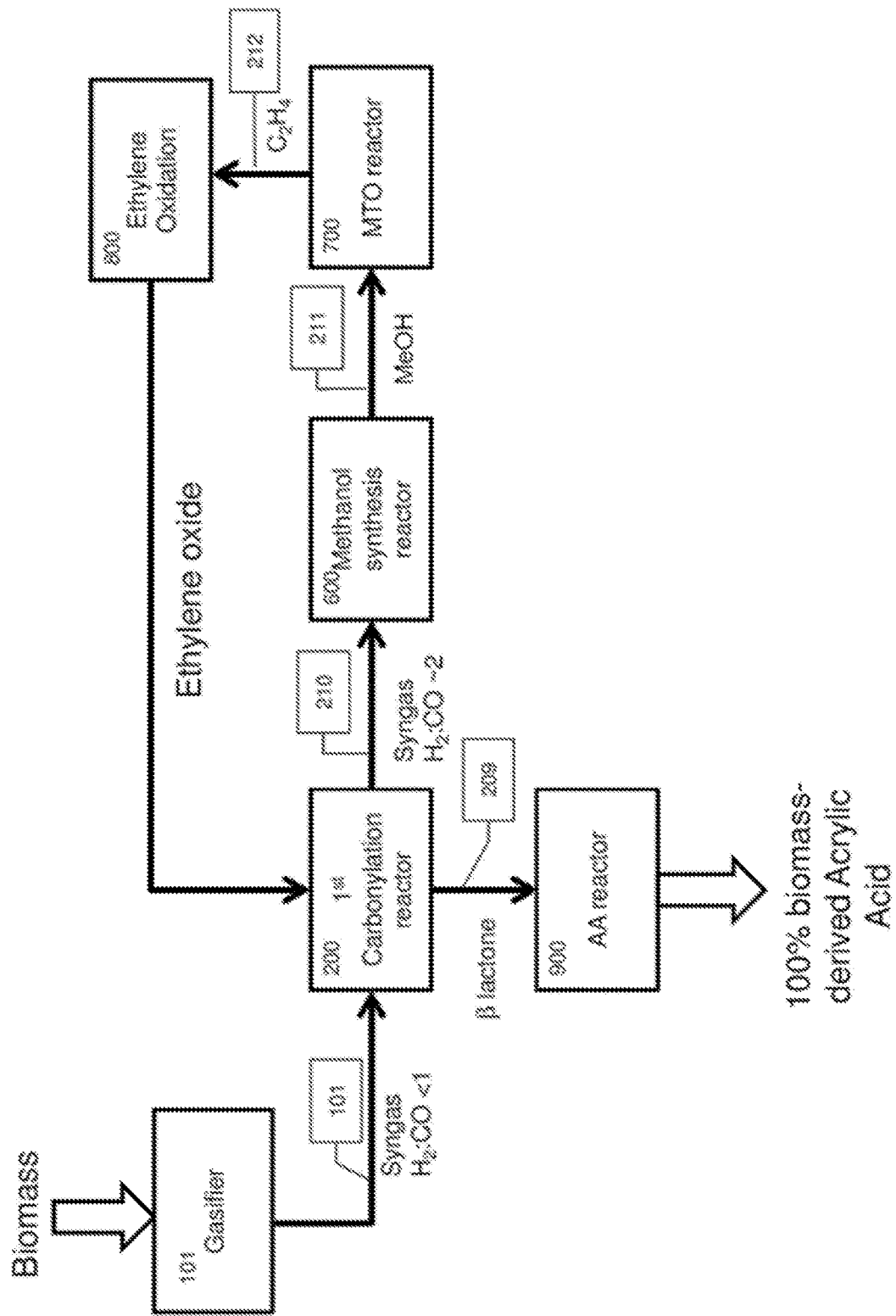
FIG. 5 shows a schematic of an exemplary process for the production of acrylic acid from biomass.
Figure 8:
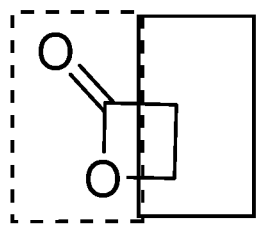
FIG. 8 shows a beta propiolactone product of the process of FIG. 5.

Therefore, in certain embodiments, provided are methods for the production of 100% biomass-derived chemicals. In certain embodiments, such chemicals are the result of the process depicted in FIG. 5. FIG. 5 shows an integrated process for production of acrylic acid from biomass. As shown, biomass is gasified in Gasifier 101 to produce a syngas stream 101 having an $H_2$:CO ratio less than 1 (typically 0.5-0.7:1). This is fed to Carbonylation Reactor 200 where it is contacted with ethylene oxide in the presence of carbonylation catalyst. Carbonylation reactor produces beta propiolactone stream 209, as shown in FIG. 8, along with upgraded syngas stream 210. Upgraded syngas stream 210 has an $H_2$ to CO ratio around 2:1 and is therefore suitable for use in methanol synthesis reactor 600. The methanol from reactor 600 is fed to MTO reactor 700 where it is converted to ethylene stream 212 (and optionally additional streams such as propylene and higher olefins, not shown). Ethylene stream 212 is directed to an oxidation reactor 800 where it is converted to ethylene oxide. The resulting ethylene oxide is fed to carbonylation reactor 200 to react with syngas stream 101.

Figure 9:
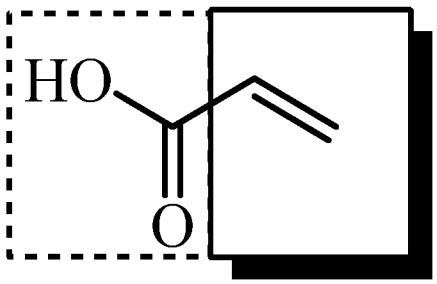
FIG. 9 shows an acrylic acid product of the process of FIG. 5

To complete the acrylic acid synthesis the beta lactone stream 209 from the carbonylation reactor is fed to AA reactor 900 where it is converted to acrylic acid. The three carbon atoms in the resulting AA are all derived from the biomass fed to reactor 101, as shown in FIG. 9.

In one aspect, provided is acrylic acid wherein all three carbon atoms are derived from biomass in an integrated gasification process characterized in that the carboxylic carbon atom is derived from CO in the syngas, and the two ethylene carbon atoms are derived from ethylene produced by MTO utilizing methanol formed from a syngas stream upgraded to increase its $H_2$ content by carbonylation of the epoxide.

A closely related process provides biomass derived polymers such as polypropiolactone (PPL) or poly(3-hydroxybutyrolactone) (PHB). Such processes either add a beta lactone polymerization reactor fed by the beta lactone stream, or utilize conditions in the carbonylation reactor to produce polyester as the primary product. For the PHB process, the MTO reactor would be operated to provide a propylene stream which is then oxidized to propylene oxide which is fed to the carbonylation reactor.

Figure 6:
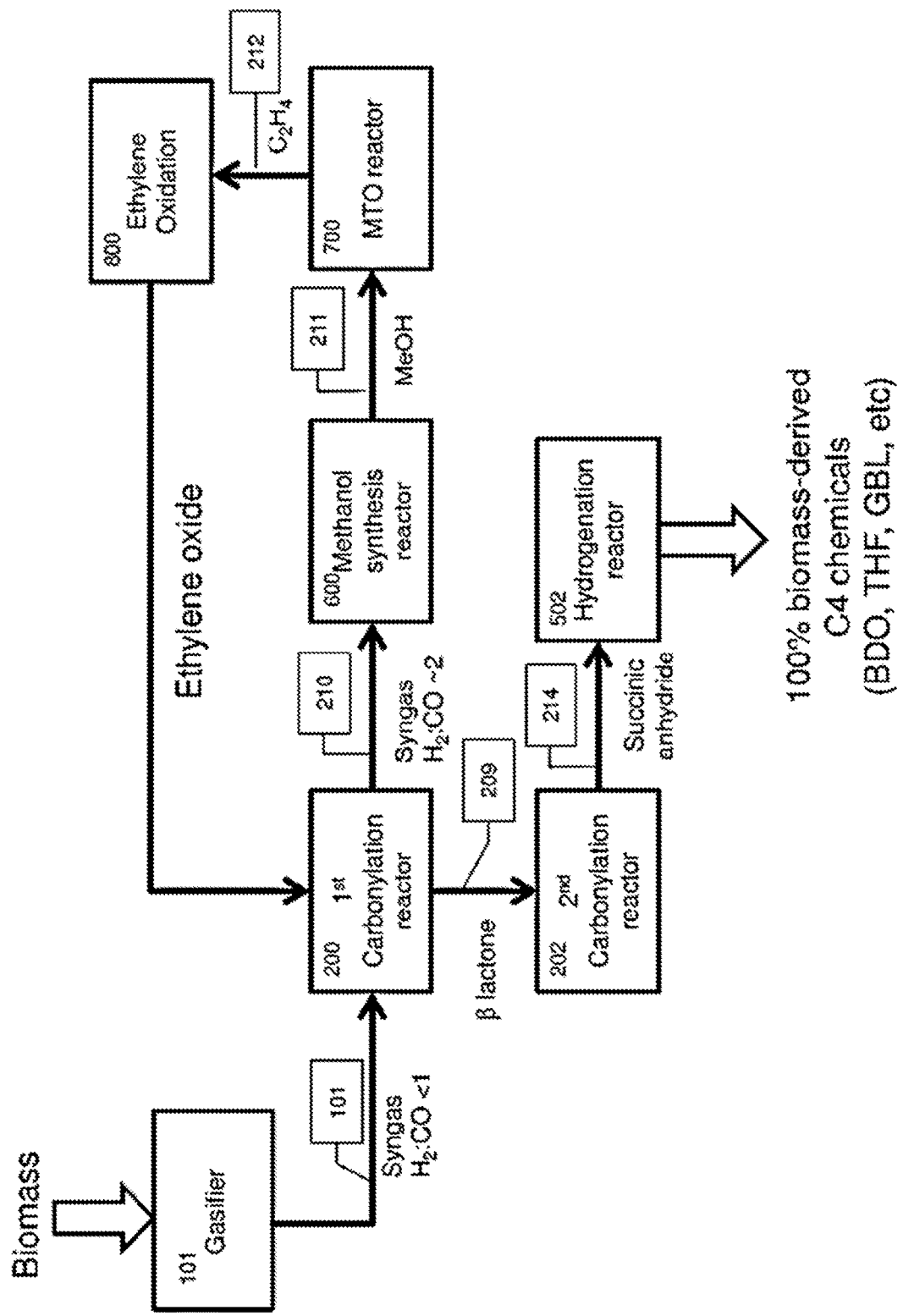
FIG. 6 shows a schematic of an exemplary process for the production of C4 chemicals from biomass.
Figure 7:
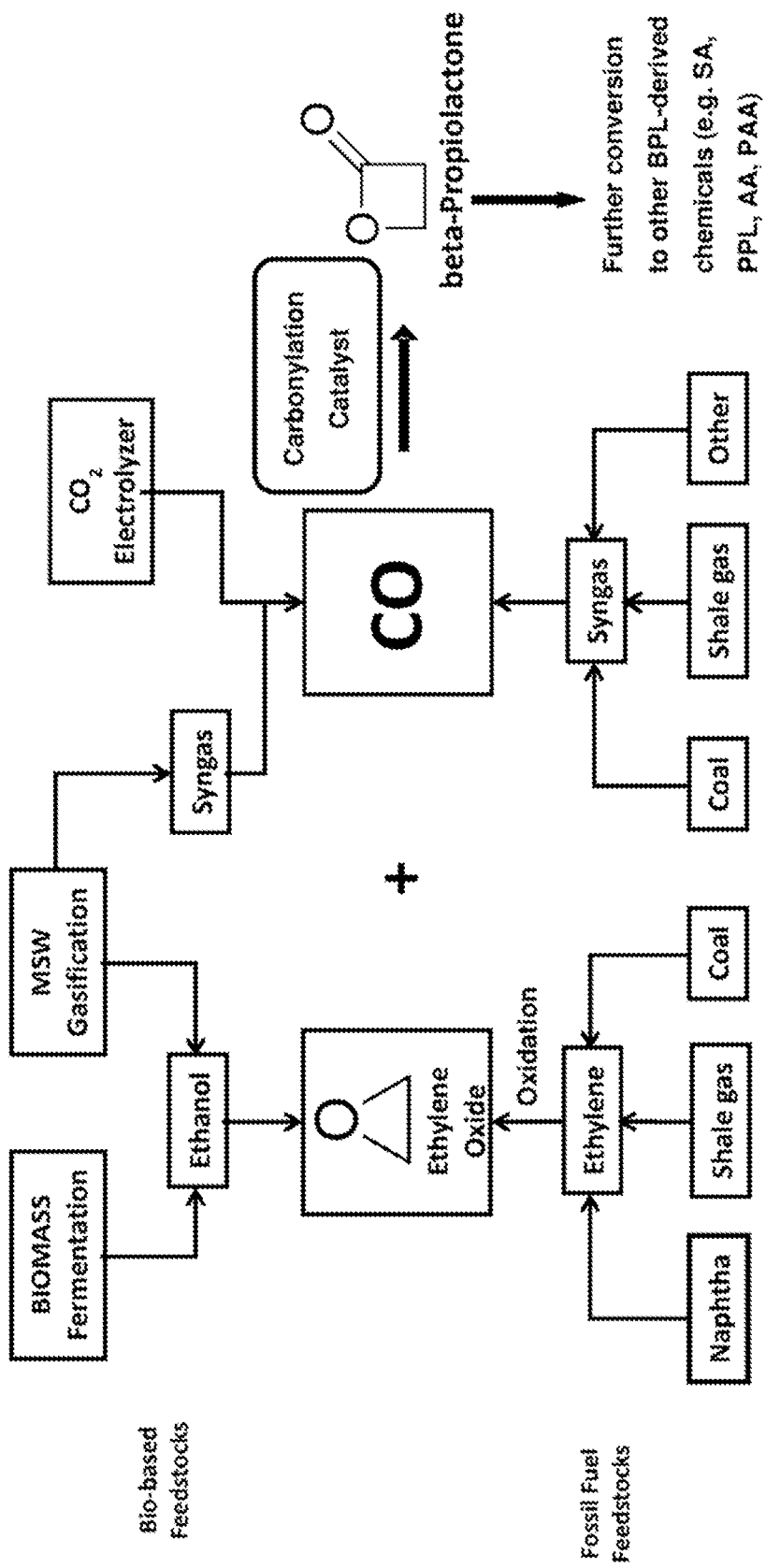
FIG. 7 shows a schematic of an exemplary process for the production of BPL and related products from both bio-based and fossil sources.
Figure 10:
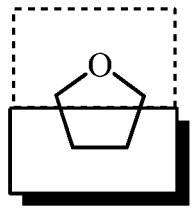
FIG. 10 shows the BDO, THF, and GBL products of the process of FIG. 6.
Figure 10:
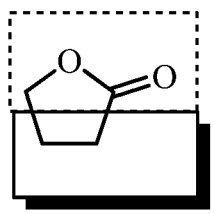
Figure 10:
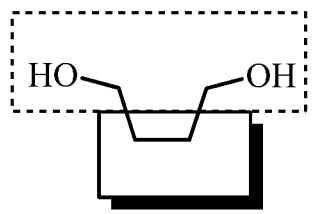

In certain other embodiments, provided are methods for the production of 100% biomass-derived C4 chemicals. In certain embodiments such chemicals are the result of the process depicted in FIG. 6. FIG. 6 shows an integrated process for production of acrylic acid from biomass. As shown, biomass is gasified in Gasifier 101 to produce a syngas stream 101 having an $H_2$:CO ratio less than 1 (typically 0.5-0.7:1). This is fed to Carbonylation Reactor 200 where it is contacted with ethylene oxide in the presence of carbonylation catalyst. Carbonylation reactor produces beta propiolactone stream 209 along with upgraded syngas stream 210. Upgraded syngas stream 210 has an $H_2$ to CO ratio around 2:1 and is therefore suitable for use in methanol synthesis reactor 600. The methanol from reactor 600 is fed to MTO reactor 700 where it is converted to ethylene stream 212 (and optionally additional streams such as propylene and higher olefins, not shown). Ethylene stream 212 is directed to an oxidation reactor 800 where it is converted to ethylene oxide. The resulting ethylene oxide is fed to carbonylation reactor 200 to react with syngas stream 101. To complete the C4 chemicals synthesis, the beta lactone stream 209 from the carbonylation reactor is fed to $2^{nd}$ carbonylation reactor 202 where it is converted to succinic anhydride. Succinic anhydride stream 214 is fed to hydrogenation reactor where it is converted to C4 commodity chemicals such as 1,4 butanediol, tetrahydrofuran, GBL, or combinations of two or more of these. The three carbon atoms in the resulting chemicals are all derived from the biomass fed to reactor 101, as shown in FIG. 10:

In one aspect, provided are C4 chemicals (such as THF, BDO and/or GBL) wherein all four carbon atoms are derived from biomass in an integrated gasification process characterized in that the carbon atoms boned to oxygen atoms are derived from CO in syngas, and the two other carbon atoms are derived from ethylene produced by MTO utilizing methanol formed from a syngas stream upgraded to increase its $H_2$ content by carbonylation of the epoxide.

In certain embodiments, the method above is characterized in that the overall process has a carbon efficiency greater than 50%. That is, at least 50% of the carbon atoms fed to the syngas production step are contained in the combined products from the EO carbonylation reactor and the methanol synthesis reactor. In certain embodiments, the method is characterized in that the overall process has a carbon efficiency greater than 55%, greater than 60%, greater than 62%, greater than 63%, greater than 64%, or greater than 65%. In certain embodiments, the method is characterized in that the overall process has a carbon efficiency greater than 66%, greater than 67%, greater than 68%, greater than 69%, or greater than 70%. In certain embodiments, the method is characterized in that the overall process has a carbon efficiency between about 50% and about 60%. In certain embodiments, the method is characterized in that the overall process has a carbon efficiency between about 55% and about 60%. In certain embodiments, the method is characterized in that the overall process has a carbon efficiency between about 60% and about 64%. In certain embodiments, the method is characterized in that the overall process has a carbon efficiency between about 64% and about 67%. In certain embodiments, the method is characterized in that the overall process has a carbon efficiency between about 67% and about 70%.

In certain embodiments, the method above is characterized in that the methanol synthesis process in step (d) is fed with syngas from the gasification process in step (a) without utilizing the water gas shift reaction to increase its $H_2$ to CO ratio.

VIII) Production of EO Carbonylation Products Having Variable Bio-Based Content

While the foregoing has focused on the use of various bio-based and fossil feedstocks for the integrated production of EO carbonylation products together with other products, the EO carbonylation technology described herein is uniquely suited for the integration of EO and CO from both bio-based and fossil sources to create EO carbonylation products containing carbon from both sources. In some embodiments, it is desirable for economic or technical reasons to have the flexibility to produce EO carbonylation products derived from both bio-based and fossil sources. The processes described herein for producing 100% bio-based content are also applicable to the production of EO carbonylation products having between 0% to 100%, (non-inclusive) bio-based content.

Figure 11:
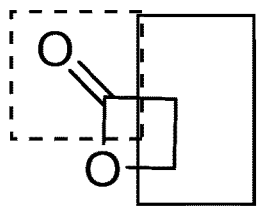
FIG. 11 shows the beta propiolactone product having biobased carbons.
Figure 12:
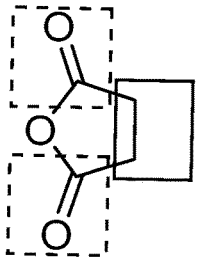
FIG. 12 shows the succinic anhydride product having biobased carbons.

In such embodiments, the resulting EO carbonylation products, including beta propiolactone, as shown in FIG. 11, and succinic anhydride, as shown in FIG. 12, may feature one or both carbonyl carbons derived from bio-based or fossil sources, and the non-carbonyl carbons derived from bio-based or fossil sources.

In some embodiments, provided is an EO carbonylation product where each carbonyl carbon is derived from a bio-based source, and the two non-carbonyl carbons are derived from a fossil source. In some embodiments, provided is an EO carbonylation product where each carbonyl carbon is derived from a fossil source, and the two non-carbonyl carbons are derived from a bio-based source. In some embodiments, provided is an EO carbonylation product where one carbonyl carbon is derived from a bio-based source, another carbonyl carbon is derived from fossil source, and the two non-carbonyl carbons are derived from a fossil source. In some embodiments, provided is an EO carbonylation product where one carbonyl carbon is derived from a bio-based source, another carbonyl carbon is derived from fossil source, and the two non-carbonyl carbons are derived from a bio-based source.

In one aspect, provided is beta propiolactone, wherein the beta propiolactone has three carbon atoms, and wherein two of the three carbon atoms in the beta propiolactone are bio-based and the third carbon atom is fossil-based. In some variations, the carbonyl carbon of the beta propiolactone is fossil-based.

In another aspect, provided is beta propiolactone, wherein the beta propiolactone has three carbon atoms, and wherein one of the three carbon atoms in the beta propiolactone is bio-based and the other two carbons atom are fossil-based. In some variations, the carbonyl carbon of the beta propiolactone is bio-based.

In yet another aspect, provided is succinic anhydride, wherein the succinic anhydride has four carbon atoms, and wherein two of the four carbon atoms of the succinic anhydride are bio-based and two of the carbon atoms are fossil-based. In some variations, the two carbonyl carbon atoms of the succinic anhydride are bio-based. In other variations, the two carbonyl carbon atoms of the succinic anhydride are fossil-based.

Examples of bio-based sources for ethylene oxide include, for example, biomass fermentation or municipal solid waste (MSW) gasification to produce ethanol which is further processed to ethylene oxide. Examples of bio-based sources of carbon monoxide include, for example, MSW gasification to produce methanol that is further processed to carbon monoxide, or electrolysis of carbon dioxide.

Examples of fossil sources for ethylene oxide include, for example, naphtha, shale gas, and coal, which can be cracked to produce ethylene, which is further processed to ethylene oxide. Examples of fossil sources for carbon monoxide include, for example, coal, oil, and shale gas, which can be processed into syngas (comprising carbon monoxide).

IX) Determination of Bio-Based Content of EO Carbonylation Products and Source Materials Bio-based content: the bio-based content of a material may be measured using the ASTM D6866 method, which allows the determination of the bio-based content of materials using radiocarbon analysis by accelerator mass spectrometry, liquid scintillation counting, and isotope mass spectrometry. When nitrogen in the atmosphere is struck by an ultraviolet light produced neutron, it loses a proton and forms carbon that has a molecular weight of 14, which is radioactive. This $^{14}C$ is immediately oxidized into carbon dioxide, and represents a small, but measurable fraction of atmospheric carbon. Atmospheric carbon dioxide is cycled by green plants to make organic molecules during photosynthesis. The cycle is completed when the green plants or other forms of life metabolize the organic molecules producing carbon dioxide which is then able to return back to the atmosphere. Virtually all forms of life on Earth depend on this green plant production of organic molecules to produce the chemical energy that facilitates growth and reproduction. Therefore, the $^{14}C$ that exists in the atmosphere becomes part of all life forms and their biological products. These renewably based organic molecules that biodegrade to carbon dioxide do not contribute to global warming because no net increase of carbon is emitted to the atmosphere. In contrast, fossil fuel-based carbon does not have the signature radiocarbon ratio of atmospheric carbon dioxide. See WO 2009/155086.

The application of ASTM D6866 to derive a "bio-based content" is built on the same concepts as radiocarbon dating, but without use of the age equations. The analysis is performed by deriving a ratio of the amount of radiocarbon ($^{14}C$) in an unknown sample to that of a modern reference standard. The ratio is reported as a percentage, with the units "pMC" (percent modern carbon). If the material being analyzed is a mixture of present day radiocarbon and fossil carbon (containing no radiocarbon), then the pMC value obtained correlates directly to the amount of bio-based material present in the sample. The modern reference standard used in radiocarbon dating is a NIST (National Institute of Standards and Technology) standard with a known radiocarbon content equivalent approximately to the year AD 1950. The year AD 1950 was chosen because it represented a time prior to thermonuclear weapons testing which introduced large amounts of excess radiocarbon into the atmosphere with each explosion (termed "bomb carbon"). The AD 1950 reference represents 100 pMC. "Bomb carbon" in the atmosphere reached almost twice normal levels in 1963 at the peak of testing and prior to the treaty halting the testing. Its distribution within the atmosphere has been approximated since its appearance, showing values that are greater than 100 pMC for plants and animals living since AD 1950. The distribution of bomb carbon has gradually decreased over time, with today's value being near 107.5 pMC. As a result, a fresh biomass material, such as corn, could result in a radiocarbon signature near 107.5 pMC.

Petroleum-based carbon does not have the signature radiocarbon ratio of atmospheric carbon dioxide. Research has noted that fossil fuels and petrochemicals have less than about 1 pMC, and typically less than about 0.1 pMC, for example, less than about 0.03 pMC. However, compounds derived entirely from renewable resources have at least about 95 percent modern carbon (pMC), they may have at least about 99 pMC, including about 100 pMC.

Combining fossil carbon with present day carbon into a material will result in a dilution of the present day pMC content. By presuming that 107.5 pMC represents present day bio-based materials and 0 pMC represents petroleum derivatives, the measured pMC value for that material will reflect the proportions of the two component types. A material derived 100% from present day biomass would give a radiocarbon signature near 107.5 pMC. If that material were diluted with 50% petroleum derivatives, it would give a radiocarbon signature near 54 pMC.

A bio-based content result is derived by assigning 100% equal to 107.5 pMC and 0% equal to 0 pMC. In this regard, a sample measuring 99 pMC will give an equivalent bio-based content result of 93%.

Assessment of the materials described herein according to the present embodiments is performed in accordance with ASTM D6866 revision 12 (i.e. ASTM D6866-12). In some embodiments, the assessments are performed according to the procedures of Method B of ASTM-D6866-12. The mean values encompass an absolute range of 6% (plus and minus 3% on either side of the bio-based content value) to account for variations in end-component radiocarbon signatures. It is presumed that all materials are present day or fossil in origin and that the desired result is the amount of bio-based carbon "present" in the material, not the amount of bio-material "used" in the manufacturing process.

Other techniques for assessing the bio-based content of materials are described in U.S. Pat. Nos. 3,885,155, 4,427,884, 4,973,841, 5,438,194, and 5,661,299, and WO2009/155086.

For example, BPL contains three carbon atoms in its structural unit. If the BPL is produced using EO and CO both from a bio-based source, then it theoretically has a bio-based content of 100%, and a pMC of 107.5, because all of the carbon atoms are derived from a renewable resource.

In some embodiments, if the BPL is produced using EO from 100% bio-based sources and CO from a fossil source, then it theoretically has a bio-based content of about 66.7% and a pMC of about 71.7, as two-thirds of the carbon atoms in the resulting BPL are derived from a bio-based source. In some embodiments, if the BPL is produced using EO from a fossil source, and CO from a bio-based source, then it theoretically has a bio-based content of about 33.3% and a pMC of about 35.8, as only one-third of the carbon atoms in the resulting BPL are derived from a bio-based source.

In some embodiments, if succinic anhydride is produced using EO from 100% bio-based sources and CO from 100% fossil sources, then it theoretically has a bio-based content of about 50% and a pMC of about 54, because half of the four carbon atoms in the resulting SA are derived from a bio-based source. In some embodiments, if succinic anhydride is produced using EO from 100% bio-based sources and one equivalent of CO from bio-based sources and one equivalent of CO from fossil sources, then it theoretically has a bio-based content of about 75% and a pMC of about 80, because three-quarters of the carbon atoms in the resulting SA are derived from a bio-based source. In some embodiments, if succinic anhydride is produced using EO from 100% fossil sources and one equivalent of CO from bio-based sources and one equivalent of CO from fossil sources, then it theoretically has a bio-based content of about 25% and a pMC of about 27, because one-quarter of the carbon atoms in the resulting SA are derived from a bio-based source.

The calculations used in the embodiments above assume that all of the EO or CO used in a given reaction step in the production of EO carbonylation products is either entirely derived from either bio-based or fossil sources. However, the methods described herein also contemplate wherein some of the EO or CO used in a given reaction step in the production of EO carbonylation products is derived from a mixture of bio-based or fossil sources, representative embodiments of which follow.

In some embodiments, if BPL is produced using EO from 50% bio-based sources and 50% fossil sources and CO from 25% bio-based sources and 75% fossil sources, then it theoretically has a bio-based content of about 41.2% and a pMC of about 44.8, as two-thirds of the carbon atoms in the resulting BPL are derived from a bio-based source.

Such a flexible system allows for the production of EO carbonylation products (and their downstream products, such as acrylic acid), containing a finely tunable percentage of bio-based material. For example, if it is important to meet certain percentages of bio-based material in BPL, but the price of one bio-based feedstock (e.g. EO) is prohibitively expensive due to market shortages, the percentage of bio-based CO can be increased to provide the same overall percentage in the final BPL product.

Traditional methods for determining the bio-based content of a sample of BPL or SA (such as those described in Methods B and C of ASTM D6866), require the complete combustion or conversion of the sample to either carbon dioxide or benzene, which are then analyzed by mass spectrometry or scintillation counting. This allows for the calculation of the overall aggregate bio-based content of the feedstocks used to produce the carbonylation products, but results in the loss of the ability to determine the bio-based content of the EO and CO feedstocks themselves. Such knowledge is useful for many reasons, including, for example, to the forensic determination of the source of a given sample of product.

A synthon is a chemical structural unit that provides one or more atoms present in the molecular structure of a product molecule. In the case of BPL or SA produced by carbonylation of EO, CO is the synthon that provides each of the carbonyl groups of BPL and SA, and EO is the synthon that provides each of the methylene ($CH_2$) carbons in BPL and SA. By extension, polypropiolactone (PPL), acrylic acid (AA), and polyacrylic acid made from BPL by this method can also be said to have their respective carbonyl carbons derived from the CO synthon, and their non-carbonyl carbons derived from the EO synthon.

In some embodiments, provided is a method for determining the bio-based content of the feedstocks by selectively degrading a sample of BPL or SA, comprising the mono-decarboxylation of the sample.

In the case of BPL, thermal decarboxylation results in the decyclization of BPL to ethylene and carbon dioxide, the ethylene fragment comprising the two carbons initially derived from EO, and the carbon dioxide comprising the one carbon initially derived from CO. Thus, the carbon dioxide produced by decarboxylation can be analyzed by methods such as Accelerator Mass Spectrometry (AMS) and Isotope Ratio Mass Spectrometry (IRMS) to determine the isotopic abundance of $^{14}C$ in the carbon dioxide, and by proxy in the CO. The ethylene can then be analyzed directly, or further combusted to carbon dioxide, then analyzed, to determine the bio-based content of the EO used to produce the BPL.

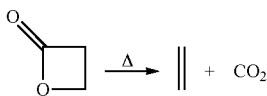

In one embodiment, provided is a method for determining whether a sample of beta-propiolactone was produced from a combination of bio-based and fossil carbon synthons, comprising:
(i) thermally decomposing the sample to ethylene and carbon dioxide;
(ii) determining the isotopic abundance of $^{14}C$ in the carbon dioxide carbon;
(iii) determining the isotopic abundance of $^{14}C$ in the ethylene carbons;
wherein, if the isotopic abundances in (ii) and (iii) are not equal, the beta-propiolactone was produced from a combination of bio-based and fossil carbon synthons.

In some embodiments, the isotopic abundance of $^{14}C$ is determined by ASTM D6866.

In the case of SA, thermal decarboxylation (which may be catalyzed by basic conditions), results in the spiro-decarboxylation of two molecules of SA to one molecule of γ-ketopimelic acid, and one molecule of carbon dioxide, which can be analyzed as in the previous paragraph to determine the bio-based content of the CO used to produce the SA. The γ-ketopimelic acid can then be combusted to carbon dioxide and analyzed to determine the bio-based content of the EO used to produce the BPL, taking into consideration that three of the seven carbons in the γ-ketopimelic acid are derived from CO. This is possible, as the bio-based content of the CO is already known from the initial decarboxylation, and so the bio-based content attributable to the EO can be determined by simple algebra.

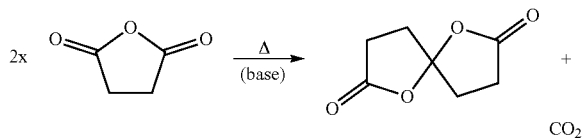

In some embodiments, provided is a method for determining whether a sample of succinic anhydride was produced from a combination of bio-based and fossil carbon synthons, comprising:
(i) thermally decomposing the sample to γ-ketopimelic acid and carbon dioxide;
(ii) determining the isotopic abundance of $^{14}C$ in the carbon dioxide carbon;
(iii) determining the isotopic abundance of $^{14}C$ in the γ-ketopimelic acid carbons;
wherein, if the isotopic abundances in (ii) and (iii) are not equal, the succinic anhydride was produced from a combination of bio-based and fossil carbon synthons.

When polyacrylic acid is heated to between 103 and 216° C. in the presence of a catalyst (copper nitrate is preferred) under an inert (preferably argon) atmosphere, it decomposes to carbon dioxide and a residue comprising a complex mixture of degradation products. See Dubinsky, et al. Polymer Degradation and Stability 86 (2004) 171-178. The exact composition of this mixture of degradation products in the residue is not important. The carbon dioxide liberated in this non-combustive decarboxylation can be analyzed as in the previous paragraphs to determine the bio-based content of the CO used to produce the polyacrylic acid. The residual degradation products are completely combusted to carbon dioxide which can then analyzed to determine the isotopic abundance of $^{14}C$. While not as exact as the procedures above for BPL and SA, a comparison of the carbon isotopic ratios for the carbon dioxide liberated during decarboxyation and that obtained from the combustion of the degradation products provides an answer as to whether the polyacrylic acid polymer was produced from a combination of bio-based and fossil carbon synthons.

In some embodiments, provided is a method for determining whether a sample of polyacrylic acid was produced from a combination of bio-based and fossil carbon synthons, comprising:
(i) thermally decomposing the sample in the presence of a copper catalyst at a temperature between 103 and 216° C. to carbon dioxide and a residue;
(ii) determining the isotopic abundance of $^{14}C$ in the carbon dioxide carbon; and
(iii) determining the isotopic abundance of $^{14}C$ in the residue, and
wherein, if the isotopic abundances in (ii) and (iii) are not equal, the polyacrylic acid was produced from a combination of bio-based and fossil carbon synthons.

Metal Carbonyl Compounds

In certain embodiments, metal carbonyl compound that may be used in the methods described herein comprises an anionic metal carbonyl moiety. In other embodiments, the metal carbonyl compound comprises a neutral metal carbonyl compound. In certain embodiments, the metal carbonyl compound comprises a metal carbonyl hydride or a hydrido metal carbonyl compound. In some embodiments, the metal carbonyl compound acts as a pre-catalyst which reacts in situ with one or more reaction components to provide an active species different from the compound initially provided. Such pre-catalysts are specifically encompassed herein, as it is recognized that the active species in a given reaction may not be known with certainty; thus the identification of such a reactive species in situ does not itself depart from the spirit or teachings herein.

In certain embodiments, the metal carbonyl compound comprises an anionic metal carbonyl species. In certain embodiments, such anionic metal carbonyl species have the general formula $[Q_dM'_e(CO)_w]^{y-}$, where Q is any ligand and need not be present, M' is a metal atom, d is an integer between 0 and 8 inclusive, e is an integer between 1 and 6 inclusive, w is a number such as to provide the stable anionic metal carbonyl complex, and y is the charge of the anionic metal carbonyl species. In certain embodiments, the anionic metal carbonyl has the general formula $[QM'(CO)_w]^{y-}$, where Q is any ligand and need not be present, M' is a metal atom, w is a number such as to provide the stable anionic metal carbonyl, and y is the charge of the anionic metal carbonyl.

In certain embodiments, the anionic metal carbonyl species include monoanionic carbonyl complexes of metals from groups 5, 7 or 9 of the periodic table or dianionic carbonyl complexes of metals from groups 4 or 8 of the periodic table. In some embodiments, the anionic metal carbonyl compound contains cobalt or manganese. In some embodiments, the anionic metal carbonyl compound contains rhodium. Suitable anionic metal carbonyl compounds include, for example, $[Co(CO)_4]^-$, $[Ti(CO)_6]^{2-}$, $[V(CO)_6]^-$, $[Rh(CO)_4]^-$, $[Fe(CO)_4]^{2-}$, $[Ru(CO)_4]^{2-}$, $[Os(CO)_4]^{2-}$, $[Cr_2(CO)_{10}]^{2-}$, $[Fe_2(CO)_8]^{2-}$, $[Tc(CO)_5]^-$, $[Re(CO)_5]^-$, and $[Mn(CO)_5]^-$. In some embodiments, the anionic metal carbonyl comprises [Co(CO)$_4$]$^-$. In some embodiments, a mixture of two or more anionic metal carbonyl complexes may be present in the polymerization system.

The term "such as to provide a stable anionic metal carbonyl" for [Q$_d$M'$_e$(CO)$_w$]$^{y-}$ is used herein to mean that [Q$_d$M'$_e$(CO)$_w$]$^{y-}$ is a species that may be characterized by analytical means, e.g., NMR, IR, X-ray crystallography, Raman spectroscopy and/or electron spin resonance (EPR) and isolable in catalyst form in the presence of a suitable cation or a species formed in situ. It is to be understood that metals which can form stable metal carbonyl complexes have known coordinative capacities and propensities to form polynuclear complexes which, together with the number and character of optional ligands Q that may be present and the charge on the complex will determine the number of sites available for CO to coordinate and therefore the value of w. Typically, such compounds conform to the "18-electron rule". Such knowledge is within the grasp of one having ordinary skill in the arts pertaining to the synthesis and characterization of metal carbonyl compounds.

In embodiments where the metal carbonyl compound is an anionic species, one or more cations must also necessarily be present. The present disclosure places no particular constraints on the identity of such cations. For example, in certain embodiments, the metal carbonyl anion is associated with a cationic Lewis acid. In other embodiments a cation associated with a provided anionic metal carbonyl compound is a simple metal cation such as those from Groups 1 or 2 of the periodic table (e.g. Na$^+$, Li$^+$, K$^+$, and Mg$^{2+}$). In other embodiments a cation associated with a provided anionic metal carbonyl compound is a bulky non electrophilic cation such as an 'onium salt' (e.g. Bu$_4$N$^+$, PPN$^+$, Ph$_4$P$^+$, and Ph$_4$As$^+$). In other embodiments, a metal carbonyl anion is associated with a protonated nitrogen compound (e.g., a cation may comprise a compound such as MeTBD-H$^+$, DMAP-H$^+$, DABCO-H$^+$, and DBU-H$^+$). In some embodiments, compounds comprising such protonated nitrogen compounds are provided as the reaction product between an acidic hydrido metal carbonyl compound and a basic nitrogen-containing compound (e.g., a mixture of DBU and HCo(CO)$_4$).

In certain embodiments, the metal carbonyl compound comprises a neutral metal carbonyl. In certain embodiments, such neutral metal carbonyl compounds have the general formula Q$_d$M'$_e$(CO)$_{w'}$, where Q is any ligand and need not be present, M' is a metal atom, d is an integer between 0 and 8 inclusive, e is an integer between 1 and 6 inclusive, and w' is a number such as to provide the stable neutral metal carbonyl complex. In certain embodiments, the neutral metal carbonyl has the general formula QM'(CO)$_{w'}$. In certain embodiments, the neutral metal carbonyl has the general formula M'(CO)$_{w'}$. In certain embodiments, the neutral metal carbonyl has the general formula QM'$_2$(CO)$_{w'}$. In certain embodiments, the neutral metal carbonyl has the general formula M'$_2$(CO)$_{w'}$. Suitable neutral metal carbonyl compounds include, for example, Ti(CO)$_7$, V$_2$(CO)$_{12}$, Cr(CO)$_6$, Mo(CO)$_6$, W(CO)$_6$, Mn$_2$(CO)$_{10}$, Tc$_2$(CO)$_{10}$, Re$_2$(CO)$_{10}$, Fe(CO)$_5$, Ru(CO)$_5$, Os(CO)$_5$, Ru$_3$(CO)$_{12}$, Os$_3$(CO)$_{12}$ Fe$_3$(CO)$_{12}$, Fe$_2$(CO)$_9$, Co$_4$(CO)$_{12}$, Rh$_4$(CO)$_{12}$, Rh$_6$(CO)$_{16}$, Ir$_4$(CO)$_{12}$, Co$_2$(CO)$_8$, and Ni(CO)$_4$.

The term "such as to provide a stable neutral metal carbonyl for Q$_d$M'$_e$(CO)$_{w'}$ is used herein to mean that Q$_d$M'$_e$(CO)$_{w'}$ is a species that may be characterized by analytical means, e.g., NMR, IR, X-ray crystallography, Raman spectroscopy and/or electron spin resonance (EPR) and isolable in pure form or a species formed in situ. It is to be understood that metals which can form stable metal carbonyl complexes have known coordinative capacities and propensities to form polynuclear complexes which, together with the number and character of optional ligands Q that may be present will determine the number of sites available for CO to coordinate and therefore the value of w'. Typically, such compounds conform to stoichiometries conforming to the "18-electron rule". Such knowledge is within the grasp of one having ordinary skill in the arts pertaining to the synthesis and characterization of metal carbonyl compounds.

In certain embodiments, one or more of the CO ligands of any of the metal carbonyl compounds described above is replaced with a ligand Q. In certain embodiments, Q is a phosphine ligand. In certain embodiments, Q is a triaryl phosphine. In certain embodiments, Q is trialkyl phosphine. In certain embodiments, Q is a phosphite ligand. In certain embodiments, Q is an optionally substituted cyclopentadienyl ligand. In certain embodiments, Q is cp. In certain embodiments, Q is cp*.

In certain embodiments, polymerization systems described herein comprise hydrido metal carbonyl compounds. In certain embodiments, such compounds are provided as the hydrido metal carbonyl compound, while in other embodiments, the hydrido metal carbonyl is generated in situ by reaction with hydrogen gas, or with a protic acid using methods known in the art (see for example *Chem. Rev.*, 1972, 72 (3), pp 231-281 DOI: 10.1021/cr60277a003).

In certain embodiments, the hydrido metal carbonyl (either as provided or generated in situ) comprises one or more of HCo(CO)$_4$, HCoQ(CO)$_3$, HMn(CO)$_5$, HMn(CO)$_4$Q, HW(CO)$_3$Q, HRe(CO)$_5$, HMo(CO)$_3$Q, HOs(CO)$_2$Q, HMo(CO)$_2$Q$_2$, HFe(CO$_2$)Q, HW(CO)$_2$Q$_2$, HRuCOQ$_2$, H$_2$Fe(CO)$_4$ or H$_2$Ru(CO)$_4$, where each Q is independently as defined above and in the classes and subclasses herein. In certain embodiments, the metal carbonyl hydride (either as provided or generated in situ) comprises HCo(CO)$_4$. In certain embodiments, the metal carbonyl hydride (either as provided or generated in situ) comprises HCo(CO)$_3$PR$_3$, where each R is independently an optionally substituted aryl group, an optionally substituted C$_{1-20}$ aliphatic group, an optionally substituted C$_{1-10}$ alkoxy group, or an optionally substituted phenoxy group. In certain embodiments, the metal carbonyl hydride (either as provided or generated in situ) comprises HCo(CO)$_3$cp, where cp represents an optionally substituted pentadienyl ligand. In certain embodiments, the metal carbonyl hydride (either as provided or generated in situ) comprises HMn(CO)$_5$. In certain embodiments, the metal carbonyl hydride (either as provided or generated in situ) comprises H$_2$Fe(CO)$_4$.

In certain embodiments, for any of the metal carbonyl compounds described above, M' comprises a transition metal. In certain embodiments, for any of the metal carbonyl compounds described above, M' is selected from Groups 5 (Ti) to 10 (Ni) of the periodic table. In certain embodiments, M' is a Group 9 metal. In certain embodiments, M' is Co. In certain embodiments, M' is Rh. In certain embodiments, M' is Ir. In certain embodiments, M' is Fe. In certain embodiments, M' is Mn.

Lewis Acidic Metal Complexes

In certain embodiments where a carbonylation catalyst is utilized in any of the methods above, the carbonylation catalyst comprises a metal carbonyl compound in combination with a cationic Lewis acid, the Lewis acid has a formula [(L$^c$)$_v$M$_b$]$^{z+}$, wherein:

L$^c$ is a ligand where, when two or more L$^c$ are present, each may be the same or different;

M is a metal atom where, when two M are present, each may be the same or different;
v is an integer from 1 to 4 inclusive;
b is an integer from 1 to 2 inclusive; and
z is an integer greater than 0 that represents the cationic charge on the metal complex.

In certain embodiments, the Lewis acids conform to structure I:

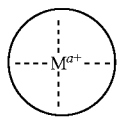

I wherein:

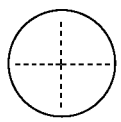

is a multidentate ligand;
M is a metal atom coordinated to the multidentate ligand;
a is the charge of the metal atom and ranges from 0 to 2; and In certain embodiments, provided metal complexes conform to structure II:

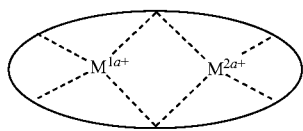

II wherein a is as defined above (each a may be the same or different), and
M$^1$ is a first metal atom;
M$^2$ is a second metal atom;

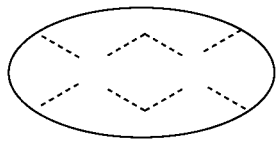

comprises a multidentate ligand system capable of coordinating both metal atoms.

For sake of clarity, and to avoid confusion between the net and total charge of the metal atoms in complexes I and II and other structures herein, the charge (a$^+$) shown on the metal atom in complexes I and II above represents the net charge on the metal atom after it has satisfied any anionic sites of the multidentate ligand. For example, if a metal atom in a complex of formula I were Cr(III), and the ligand were porphyrin (a tetradentate ligand with a charge of −2), then the chromium atom would have a net charge of +1, and a would be 1.

Suitable multidentate ligands include, for example, porphyrin ligands 1, salen ligands 2, dibenzotetramethyltetraaza[14]annulene (tmtaa) ligands 3, phthalocyaninate ligands 4, Trost ligand 5, tetraphenylporphyrin ligands 6, and corrole ligands 7. In certain embodiments, the multidentate ligand is a salen ligands. In other embodiments, the multidentate ligand is a porphyrin ligands. In other embodiments, the multidentate ligand is a tetraphenylporphyrin ligands. In other embodiments, the multidentate ligand is a corrole ligands. Any of the foregoing ligands can be unsubstituted or can be substituted. Numerous variously substituted analogs of these ligands are known in the art and will be apparent to the skilled artisan.

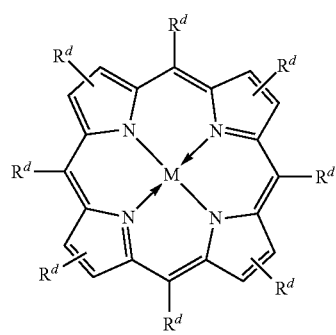

1

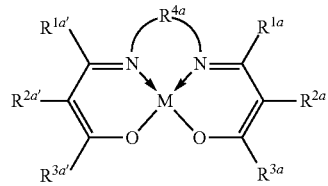

2

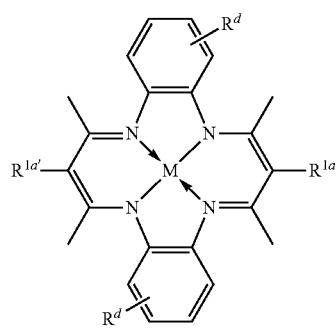

3

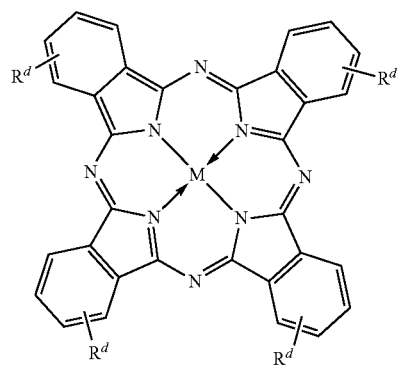

4

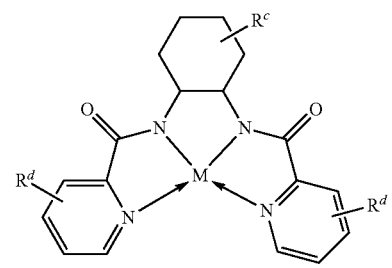

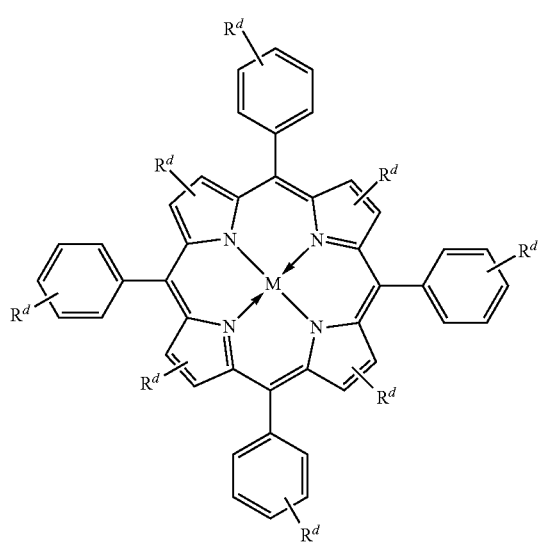

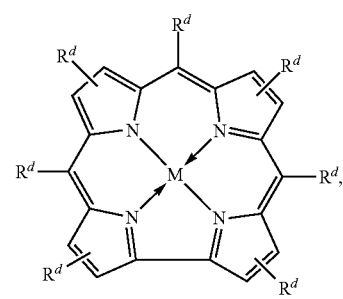

wherein each of $R^c$, $R^d$, $R^a$, $R^{1a}$, $R^{2a}$, $R^{3a}$, $R^{1a'}$, $R^{2a'}$, $R^{3a'}$, and M, is as defined and described in the classes and subclasses herein.

In certain embodiments, Lewis acids provided in polymerization systems described herein comprise metal-porphinato complexes. In certain embodiments, the moiety

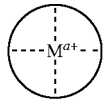

has the structure:

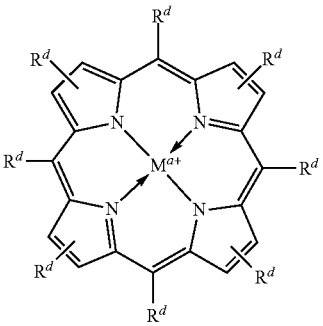

wherein each of M and a is as defined above and described in the classes and subclasses herein, and $R^d$ at each occurrence is independently hydrogen, halogen, —OR⁴, —NR$^y$₂, —SR$^y$, —CN, —NO₂, —SO₂R$^y$, —SOR$^y$, —SO₂NR$^y$₂; —CNO, —NR$^y$SO₂R$^y$, —NCO, —N₃, —SiR$^y$₃; or an optionally substituted group selected from the group consisting of C$_{1-20}$ aliphatic; C$_{1-20}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, and sulfur; and 4- to 7-membered heterocyclic having 1-2 heteroatoms independently selected from the group consisting of nitrogen, oxygen, and sulfur, where two or more R$^d$ groups may be taken together to form one or more optionally substituted rings, where each R$^y$ is independently hydrogen, an optionally substituted group selected the group consisting of acyl; carbamoyl, arylalkyl; 6- to 10-membered aryl; C$_{1-12}$ aliphatic; C$_{1-12}$ heteroaliphatic having 1-2 heteroatoms independently selected from the group consisting of nitrogen, oxygen, and sulfur; 5- to 10-membered heteroaryl having 1-4 heteroatoms independently selected from the group consisting of nitrogen, oxygen, and sulfur; 4- to 7-membered heterocyclic having 1-2 heteroatoms independently selected from the group consisting of nitrogen, oxygen, and sulfur; an oxygen protecting group; and a nitrogen protecting group; two R$^y$ on the same nitrogen atom are taken with the nitrogen atom to form an optionally substituted 4- to 7-membered heterocyclic ring having 0-2 additional heteroatoms independently selected from the group consisting of nitrogen, oxygen, and sulfur; and each R⁴ independently is a hydroxyl protecting group or R$^y$.

In certain embodiments, the moiety

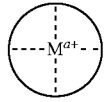

has the structure:

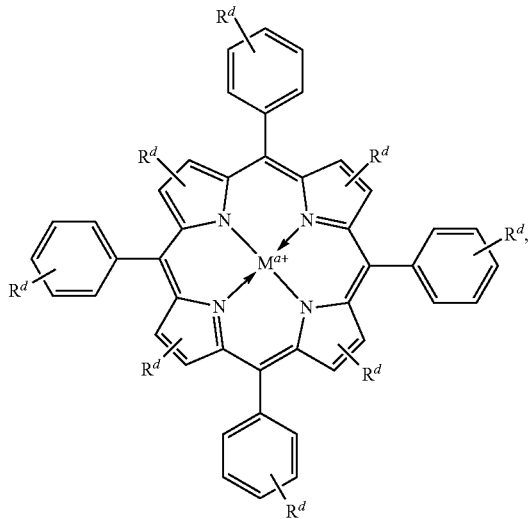

where M, a and $R^d$ are as defined above and in the classes and subclasses herein.

In some embodiments, the carbonylation catalyst includes a carbonyl cobaltate in combination with an aluminum porphyrin compound. In some embodiments, the carbonylation catalyst is [(TPP)Al(THF)$_2$][Co(CO)$_4$] where TPP stands for tetraphenylporphyrin and THF stands for tetrahydrofuran.

In certain embodiments, the moiety

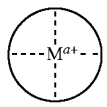

has the structure:

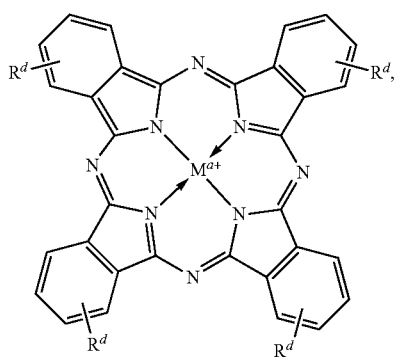

where M, a and $R^d$ are as defined above and in the classes and subclasses herein.

In certain embodiments, Lewis acids included in polymerization systems herein comprise metallo salenate complexes. In certain embodiments, the moiety

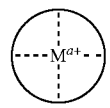

has the structure:

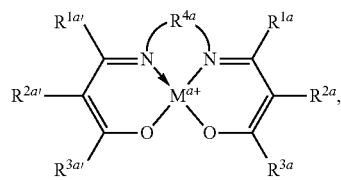

wherein:

M, and a are as defined above and in the classes and subclasses herein.

$R^{1a}$, $R^{1a'}$, $R^{2a}$, $R^{2a'}$, $R^{3a}$, and $R^{3a'}$ are independently hydrogen, halogen, —OR$^4$, —NR$^y_2$, —SR$^y$, —CN, —NO$_2$, —SO$_2$R$^y$, —SOR$^y$, —SO$_2$NR$^y_2$; —CNO, —NRSO$_2$R$^y$, —NCO, —N$_3$, —SiR$^y_3$; or an optionally substituted group selected from the group consisting of C$_{1-20}$ aliphatic; C$_{1-20}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, and sulfur; and 4- to 7-membered heterocyclic having 1-2 heteroatoms independently selected from the group consisting of nitrogen, oxygen, and sulfur; wherein each $R^4$, and $R^y$ is independently as defined above and described in classes and subclasses herein, wherein any of ($R^{2a'}$ and $R^{3a'}$), ($R^{2a}$ and $R^{3a}$), ($R^{1a}$ and $R^{2a}$), and ($R^{1a'}$ and $R^{2a'}$) may optionally be taken together with the carbon atoms to which they are attached to form one or more rings which may in turn be substituted with one or more R groups; and $R^{4a}$ is selected from the group consisting of:

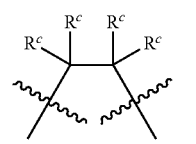 e)

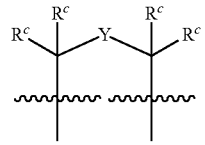 f)

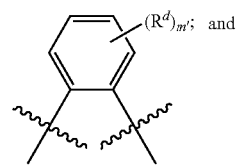 g)

-continued h)

where
R$^c$ at each occurrence is independently hydrogen, halogen, —OR$^4$, —NR$^y{}_2$, —SR$^y$, —CN, —NO$_2$, —SO$_2$R$^y$, —SOR$^y$, —SO$_2$NR$^y{}_2$; —CNO, —NR$^y$SO$_2$R$^y$, —NCO, —N$_3$, —SiR$^y{}_3$; or an optionally substituted group selected from the group consisting of C$_{1-20}$ aliphatic; C$_{1-20}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, and sulfur; and 4- to 7-membered heterocyclic having 1-2 heteroatoms independently selected from the group consisting of nitrogen, oxygen, and sulfur;
where:
two or more R$^c$ groups may be taken together with the carbon atoms to which they are attached and any intervening atoms to form one or more rings;
when two R$^c$ groups are attached to the same carbon atom, they may be taken together along with the carbon atom to which they are attached to form a moiety selected from the group consisting of: a 3- to 8-membered spirocyclic ring, a carbonyl, an oxime, a hydrazone, an imine; and an optionally substituted alkene;
Y is a divalent linker selected from the group consisting of: —NR$^y$—, —N(R$^y$)C(O)—, —C(O)NR$^y$—, —O—, —C(O)—, —OC(O)—, —C(O)O—, —S—, —SO—, —SO$_2$—, —C(=S)—, —C(=NR$^y$)—, —N=N—; a polyether; a C$_3$ to C$_8$ substituted or unsubstituted carbocycle; and a C$_1$ to C$_8$ substituted or unsubstituted heterocycle;
m' is 0 or an integer from 1 to 4, inclusive;
q is 0 or an integer from 1 to 4, inclusive; and
x is 0, 1, or 2.

In certain embodiments, a provided Lewis acid comprises a metallo salen compound, as shown in formula Ia:

Ia wherein each of M, R$^d$, and a, is as defined above and in the classes and subclasses herein, represents is an optionally substituted moiety linking the two nitrogen atoms of the diamine portion of the salen ligand, where is selected from the group consisting of a C$_3$-C$_{14}$ carbocycle, a C$_6$-C$_{10}$ aryl group, a C$_3$-C$_{14}$ heterocycle, and a C$_5$-C$_{10}$ heteroaryl group; or an optionally substituted C$_{2-20}$ aliphatic group, wherein one or more methylene units are optionally and independently replaced by —NR$^y$—, —N(R$^y$)C(O)—, —C(O)N(R$^y$)—, —OC(O)N(R$^y$)—, —N(R$^y$)C(O)O—, —OC(O)O—, —O—, —C(O)—, —OC(O)—, —C(O)O—, —S—, —SO—, —SO$_2$—, —C(=S)—, —C(=NR$^y$)—, —C(=NOR$^y$)— or —N=N—.

In certain embodiments metal complexes having formula Ia above, at least one of the phenyl rings comprising the salicylaldehyde-derived portion of the metal complex is independently selected from the group consisting of:

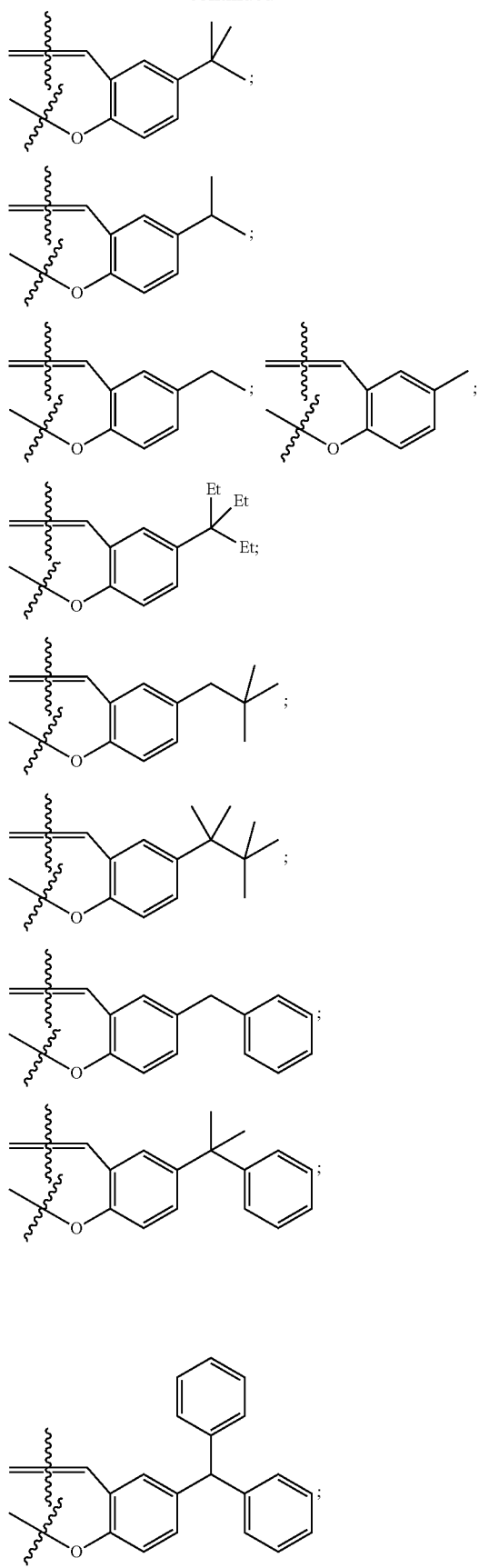
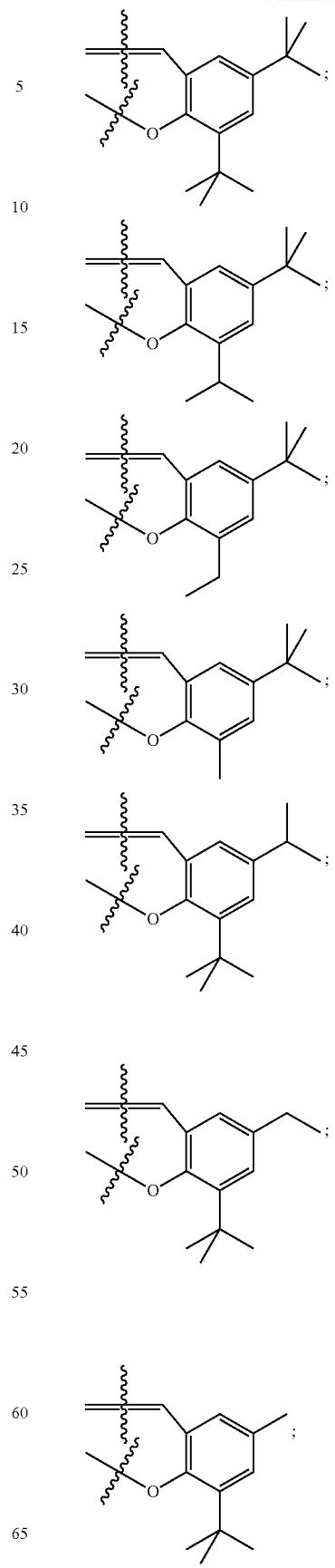

-continued

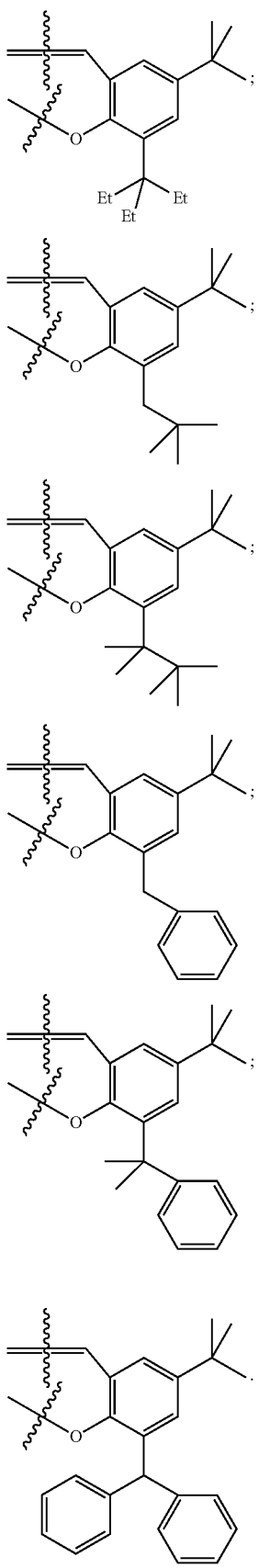

In certain embodiments, a provided Lewis acid comprises a metallo salen compound, conforming to one of formulae Va or Vb:

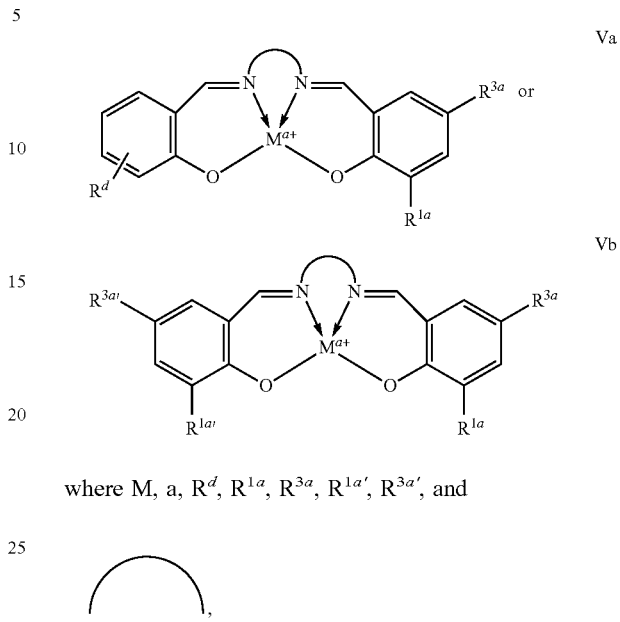

where M, a, $R^d$, $R^{1a}$, $R^{3a}$, $R^{1a\prime}$, $R^{3a\prime}$, and

are as defined above and in the classes and subclasses herein.

In certain embodiments of metal complexes having formulae Va or Vb, each $R^{1a}$ and $R^{3a}$ is, independently, optionally substituted $C_1$-$C_{20}$ aliphatic.

In certain embodiments, the moiety

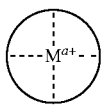

comprises an optionally substituted 1,2-phenyl moiety.

In certain embodiments, Lewis acids included in polymerization systems herein comprise metal-tmtaa complexes. In certain embodiments, the moiety

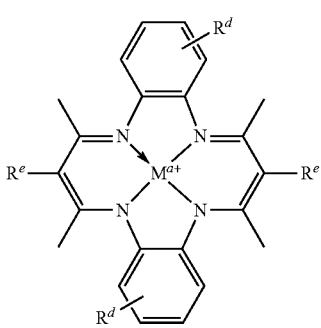

has the structure:

where M, a and $R^d$ are as defined above and in the classes and subclasses herein, and $R^e$ at each occurrence is independently hydrogen, halogen, —$OR^4$, —$NR^y_2$, —$SR^y$, —CN, —$NO_2$, —$SO_2R^y$, —$SOR^y$, —$SO_2NR^y_2$; —CNO, —$NR^ySO_2R^y$, —NCO, —$N_3$, —$SiR^y_3$; or an optionally substituted group selected from the group consisting of $C_{1-20}$ aliphatic; $C_{1-20}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, and sulfur; and 4- to 7-membered heterocyclic having 1-2 heteroatoms independently selected from the group consisting of nitrogen, oxygen, and sulfur.

In certain embodiments, the moiety

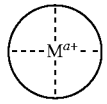

has the structure:

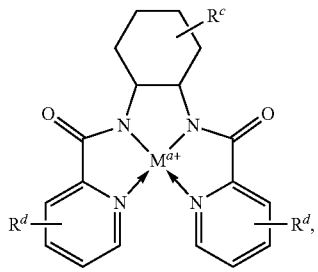

where each of M, a, $R^c$ and $R^d$ is as defined above and in the classes and subclasses herein.

In certain embodiments, where polymerization systems herein include a Lewis acidic metal complex, the metal atom is selected from the periodic table groups 2-13, inclusive. In certain embodiments, M is a transition metal selected from the periodic table groups 4, 6, 11, 12 and 13. In certain embodiments, M is aluminum, chromium, titanium, indium, gallium, zinc cobalt, or copper. In certain embodiments, M is aluminum. In other embodiments, M is chromium.

In certain embodiments, M has an oxidation state of +2. In certain embodiments, M is Zn(II), Cu(II), Mn(II), Co(II), Ru(II), Fe(II), Co(II), Rh(II), Ni(II), Pd(II) or Mg(II). In certain embodiments M is Zn(II). In certain embodiments M is Cu(II).

In certain embodiments, M has an oxidation state of +3. In certain embodiments, M is Al(III), Cr(III), Fe(III), Co(III), Ti(III) In(III), Ga(III) or Mn(III). In certain embodiments M is Al(III). In certain embodiments M is Cr(III).

In certain embodiments, M has an oxidation state of +4. In certain embodiments, M is Ti(IV) or Cr(IV).

In certain embodiments, $M^1$ and $M^2$ are each independently a metal atom selected from the periodic table groups 2-13, inclusive. In certain embodiments, M is a transition metal selected from the periodic table groups 4, 6, 11, 12 and 13. In certain embodiments, M is aluminum, chromium, titanium, indium, gallium, zinc cobalt, or copper. In certain embodiments, M is aluminum. In other embodiments, M is chromium. In certain embodiments, $M^1$ and $M^2$ are the same. In certain embodiments, $M^1$ and $M^2$ are the same metal, but have different oxidation states. In certain embodiments, $M^1$ and $M^2$ are different metals.

In certain embodiments, one or more of $M^1$ and $M^2$ has an oxidation state of +2. In certain embodiments, $M^1$ is Zn(II), Cu(II), Mn(II), Co(II), Ru(II), Fe(II), Co(II), Rh(II), Ni(II), Pd(II) or Mg(II). In certain embodiments $M^1$ is Zn(II). In certain embodiments $M^1$ is Cu(II). In certain embodiments, $M^2$ is Zn(II), Cu(II), Mn(II), Co(II), Ru(II), Fe(II), Co(II), Rh(II), Ni(II), Pd(II) or Mg(II). In certain embodiments $M^2$ is Zn(II). In certain embodiments $M^2$ is Cu(II).

In certain embodiments, one or more of $M^1$ and $M^2$ has an oxidation state of +3. In certain embodiments, $M^1$ is Al(III), Cr(III), Fe(III), Co(III), Ti(III) In(III), Ga(III) or Mn(III). In certain embodiments $M^1$ is Al(III). In certain embodiments $M^1$ is Cr(III). In certain embodiments, $M^2$ is Al(III), Cr(III), Fe(III), Co(III), Ti(III) In(III), Ga(III) or Mn(III). In certain embodiments $M^2$ is Al(III). In certain embodiments $M^2$ is Cr(III).

In certain embodiments, one or more of $M^1$ and $M^2$ has an oxidation state of +4. In certain embodiments, $M^1$ is Ti(IV) or Cr(IV). In certain embodiments, $M^2$ is Ti(IV) or Cr(IV).

In certain embodiments, one or more neutral two electron donors coordinate to M $M^1$ or $M^2$ and fill the coordination valence of the metal atom. In certain embodiments, the neutral two electron donor is a solvent molecule. In certain embodiments, the neutral two electron donor is an ether. In certain embodiments, the neutral two electron donor is tetrahydrofuran, diethyl ether, acetonitrile, carbon disulfide, or pyridine. In certain embodiments, the neutral two electron donor is tetrahydrofuran. In certain embodiments, the neutral two electron donor is an epoxide. In certain embodiments, the neutral two electron donor is an ester or a lactone.

It is claimed:

1. A method for creating a composition of beta-propiolactone or succinic anhydride comprising:
   carbonylating ethylene oxide using carbon monoxide;
   wherein at least one of the ethylene oxide or the carbon monoxide has a bio-based carbon content greater than zero percent and a pMC greater than zero, and optionally at least one of the ethylene oxide or the carbon monoxide has a fossil-based carbon content;
   to produce beta-propiolactone with a pMC of about 35.8 to about 107.5, or succinic anhydride with a pMC of about 27 to about 107.5.

2. The method of claim 1, wherein the carbon monoxide has a pMC of 107.5 or the ethylene oxide has a pMC of 107.5.

3. The method of claim 1, wherein one of the ethylene oxide and carbon monoxide has a bio-based carbon content greater than zero percent, and the other has a bio-based carbon content of less than 100 percent.

4. The method of claim 3, wherein the ethylene oxide has a bio-based carbon content of 100 percent or the carbon monoxide has a bio-based carbon content of 100 percent.

5. The method of claim 1, wherein the beta-propiolactone has three carbon atoms;
   wherein two of the three carbon atoms in the beta-propiolactone are bio-based carbon and the third carbon atom is fossil-based carbon; and
   wherein the beta-propiolactone has a pMC of about 71.7.

6. The method of claim 5, wherein the carbonyl carbon of the beta-propiolactone is fossil-based carbon.

7. The method of claim 1, wherein the beta-propiolactone has three carbon atoms;
wherein one of the three carbon atoms in the beta-propiolactone is bio-based carbon and the other two carbons atom are fossil-based carbon; and
wherein the beta-propiolactone has a pMC of about 35.8.

8. The method of claim 7, wherein the carbonyl carbon of the beta-propiolactone is bio-based carbon.

9. The method of claim 1, wherein the succinic anhydride has four carbon atoms;
wherein two of the four carbon atoms of the succinic anhydride are bio-based carbon and two of the carbon atoms are fossil-based carbon; and
wherein the succinic anhydride has a pMC of about 54.

10. The method of claim 9, wherein the two carbonyl carbon atoms of the succinic anhydride are bio-based carbon.

11. The method of claim 9, wherein the two carbonyl carbon atoms of the succinic anhydride are fossil-based carbon.

12. A composition comprising:
beta-propiolactone having bio-based carbon, and optionally fossil-based carbon;
wherein the beta-propiolactone has a pMC of about 35.8 to about 107.5.

13. The composition of claim 12, wherein the beta-propiolactone has three carbon atoms;
wherein the carbon atoms are bio-based carbon and fossil-based carbon; and
wherein the beta-propiolactone has a pMC of about 35.8 to about 71.7.

14. The composition of claim 13, wherein two of the three carbon atoms are bio-based carbon and the third carbon atom is fossil-based carbon; and
wherein the beta-propiolactone has a pMC of about 71.7.

15. The composition of claim 13, wherein two of the three carbon atoms are fossil-based carbon and the third carbon atom is bio-based carbon; and
wherein the beta-propiolactone has a pMC of about 35.8.

16. A composition comprising:
succinic anhydride having bio-based carbon, and optionally fossil-based carbon;
wherein the succinic anhydride has a pMC of about 27 to about 107.5.

17. The composition of claim 16, wherein the succinic anhydride has four carbon atoms:
wherein the carbon atoms are bio-based carbon and fossil-based carbon; and
wherein the succinic anhydride has a pMC of about 27 to about 80.

18. The composition of claim 17, wherein two of the four carbon atoms of the succinic anhydride are bio-based carbon and two of the carbon atoms are fossil-based carbon; and
wherein the succinic anhydride has a pMC of about 54.

19. The composition of claim 17, wherein three of the four carbon atoms of the succinic anhydride are bio-based carbon and one of the carbon atoms is fossil-based carbon; and
wherein the succinic anhydride has a pMC of about 80.

20. The composition of claim 17, wherein three of the four carbon atoms of the succinic anhydride are fossil-based carbon and one of the carbon atoms is bio-based carbon; and
wherein the succinic anhydride has a pMC of about 27.

* * * * *

UNITED STATES PATENT AND TRADEMARK OFFICE
CERTIFICATE OF CORRECTION

PATENT NO. : 11,807,613 B2
APPLICATION NO. : 17/386627
DATED : November 7, 2023
INVENTOR(S) : Sadesh H. Sookraj et al.

It is certified that error appears in the above-identified patent and that said Letters Patent is hereby corrected as shown below:

In the Claims

Column 57, Claim 7, Line 5, "carbons atom" should be —carbon atoms—

Signed and Sealed this
Nineteenth Day of March, 2024

Katherine Kelly Vidal
*Director of the United States Patent and Trademark Office*